US008952029B2

(12) United States Patent
Eller

(10) Patent No.: US 8,952,029 B2
(45) Date of Patent: *Feb. 10, 2015

(54) METHOD OF ADMINISTRATION OF GAMMA HYDROXYBUTYRATE WITH MONOCARBOXYLATE TRANSPORTERS

(71) Applicant: Jazz Pharmaceuticals Ireland Limited, Dublin (IE)

(72) Inventor: Mark Eller, Redwood City, CA (US)

(73) Assignee: Jazz Pharmaceuticals Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/873,000

(22) Filed: Apr. 29, 2013

(65) Prior Publication Data

US 2014/0249222 A1    Sep. 4, 2014

Related U.S. Application Data

(63) Continuation of application No. 13/837,714, filed on Mar. 15, 2013.

(60) Provisional application No. 61/771,557, filed on Mar. 1, 2013, provisional application No. 61/777,873, filed on Mar. 12, 2013.

(51) Int. Cl.
| | |
|---|---|
| *A61K 31/33* | (2006.01) |
| *A61K 31/19* | (2006.01) |
| *A61K 31/505* | (2006.01) |
| *A61K 31/55* | (2006.01) |
| *A61K 31/616* | (2006.01) |

(52) U.S. Cl.
CPC ................ *A61K 31/19* (2013.01); *A61K 31/33* (2013.01); *A61K 31/505* (2013.01); *A61K 31/55* (2013.01); *A61K 31/616* (2013.01)
USPC ........................ 514/275; 514/183; 514/214.03

(58) Field of Classification Search
USPC .................................................... 514/188.3
See application file for complete search history.

(56) References Cited

U.S. PATENT DOCUMENTS

| | | | |
|---|---|---|---|
| 3,325,361 A | 6/1967 | Meunier | |
| 3,385,886 A | 5/1968 | Nicholson et al. | |
| 4,155,929 A | 5/1979 | Chignac et al. | |
| 4,393,236 A | 7/1983 | Klosa | |
| 5,380,937 A | 1/1995 | Koehler et al. | |
| 5,758,095 A | 5/1998 | Albaum et al. | |
| 5,833,599 A | 11/1998 | Schrier et al. | |
| 5,845,255 A | 12/1998 | Mayaud | |
| 6,014,631 A | 1/2000 | Teagarden et al. | |
| 6,067,524 A | 5/2000 | Byerly et al. | |
| 6,112,182 A | 8/2000 | Akers et al. | |
| 6,204,245 B1 * | 3/2001 | Siegel et al. | 514/17.7 |
| 6,317,719 B1 | 11/2001 | Schrier et al. | |
| 6,356,873 B1 | 3/2002 | Teagarden et al. | |
| 6,472,431 B2 * | 10/2002 | Cook et al. | 514/557 |
| 6,780,889 B2 | 8/2004 | Cook et al. | |
| 7,015,200 B2 | 3/2006 | Mamelak et al. | |
| 7,072,840 B1 | 7/2006 | Mayaud | |
| 7,262,219 B2 | 8/2007 | Cook et al. | |
| 7,572,605 B2 | 8/2009 | Mamelak et al. | |
| 7,668,730 B2 | 2/2010 | Reardan et al. | |
| 7,765,106 B2 | 7/2010 | Reardan et al. | |
| 7,765,107 B2 | 7/2010 | Reardan et al. | |
| 7,797,171 B2 | 9/2010 | Reardan et al. | |
| 7,851,506 B2 | 12/2010 | Cook et al. | |
| 7,895,059 B2 | 2/2011 | Reardan et al. | |
| 8,263,650 B2 | 9/2012 | Cook et al. | |
| 8,324,275 B2 | 12/2012 | Cook et al. | |
| 2003/0171270 A1 | 9/2003 | Civelli et al. | |
| 2006/0018933 A1 | 1/2006 | Vaya et al. | |
| 2008/0293698 A1 | 11/2008 | Johnson | |
| 2009/0137565 A1 | 5/2009 | Frucht | |
| 2010/0112056 A1 | 5/2010 | Rourke et al. | |
| 2010/0160299 A1 | 6/2010 | Baker, Jr. et al. | |
| 2011/0237664 A1 | 9/2011 | Dalton et al. | |
| 2012/0076865 A1 | 3/2012 | Allphin et al. | |

FOREIGN PATENT DOCUMENTS

| | | |
|---|---|---|
| DE | 237 309 | 5/1985 |
| GB | 922 029 | 3/1963 |
| GB | 980 279 | 1/1965 |
| GB | 1 522 450 | 8/1978 |
| WO | WO 2006/053186 | 5/2006 |
| WO | WO 2010/053691 | 5/2010 |
| WO | WO 2011/119839 | 9/2011 |

(Continued)

OTHER PUBLICATIONS

Tonussi et al (Eur. J. Pharmacol (1994) 14; 251 (2-3):173-9 Abstract Only).*
United States Patent and Trademark Office, Office Action mailed Sep. 13, 2013, in related U.S. Appl. No. 13/872,997.
U.S. Appl. No. 13/739,886, filed Jan. 11, 2013, Allphin et al.
U.S. Appl. No. 61/317,212, filed Mar. 24, 2010, Allphin et al.
Arena et al., "Absorption of Sodium γ-Hydroxybutyrate and Its Prodrug γ-Butyrolactone: Relationship between In Vitro Transport and In Vivo Absorption," *J. Pharmaceutical Sciences*,69(3): 356-358, 1980.
Auler et al., "Diclofenac Plasma Protein Binding: PK-PD Modelling in Cardiac Patients Submitted to Cardiopulmonary Bypass," *Braz. J Med. Bio. Res.*, 30: 369-374, 1997.
Banerjee et al., "Presynaptic *Gamma* -Hydroxybutyric Acid (GHB) and *Gamma* -Aminobutyric Acid$_B$ (GABA$_B$) Receptor-Mediated Release of GABA and glutamate (GLU) in Rat Thalamic Ventrobasal Nucleus (VB): A Possible Mechanism for the Generation of Absence-Like Seizures Induced by GHB," *J. Pharmacol. Exp. Ther.*, 273 (3): 1534-1543, 1995.

(Continued)

*Primary Examiner* — Shirley V Gembeh
(74) *Attorney, Agent, or Firm* — Jones Day

(57) ABSTRACT

One embodiment of the present invention is to improve the safety and efficacy of the administration of GHB or a salt thereof to a patient. It has been discovered that the concomitant administration of an MCT inhibitor, such as diclofenac, valproate, or ibuprofen, will affect GHB administration. For example, it has been discovered that diclofenac lowers the effect of GHB in the body, thereby potentially causing an unsafe condition. Furthermore, it has been discovered that valproate increases the effect of GHB on the body, thereby potentially causing an unsafe condition.

28 Claims, 10 Drawing Sheets

(56) References Cited

FOREIGN PATENT DOCUMENTS

| WO | WO 2011/139271 | 11/2011 |
|---|---|---|
| WO | WO 2012/037457 | 3/2012 |

OTHER PUBLICATIONS

Bédard et al., "Nocturnal γ-Hydroxybutyrate. Effect on Periodic Leg Movements and Sleep Organization of Narcoleptic Patients," *Clin. Neuropharmacol.*, 12(1): 29-36, 1989.
Broughton et al., "The Treatment of Narcolepsy-Cataplexy with Nocturnal Gamma-Hydroxybutyrate," *Le Journal Canadien Des Sciences Neurologiques*, 6(1): 1-6, 1979.
Cash et al., "γ-Hydroxybutyrate Receptor Function Studied by the Modulation of Nitric Oxide Synthase Activity in Rat Frontal Cortex Punches," *Biochemical Pharmacology*, 58 (11): 1815-1819, 1999.
Dimitrijevic et al., "*Drosophila* GABA$_B$ Receptors are Involved in Behavioral Effects of γ-Hydroxybutyric Acid (GHB)," *Eur. J. Pharmacol.*, 519 (3): 246-252, 2005.
Gallimberti et al., "Gamma-Hydroxybutyric Acid for Treatment of Alcohol Withdrawal Syndrome," *The Lancet*, Sep. 30: 787-789, 1989.
Gallimberti et al., "Gamma-Hydroxybutyric Acid in the Treatment of Alcohol Dependence: A Double-Blind Study," *Alcoholism: Clinical and Experimental Research*, 16(4): 673-676, 1992.
Gallimberti et al., "Gamma-Hydroxybutyric Acid for Treatment of Opiate Withdrawal Syndrome," *Neuropsychopharmacology*, 9(1): 77-81, 1993.
Gallimberti et al., "Clinical Efficacy of Gamma-Hydroxybutyric Acid in Treatment of Opiate Withdrawal," *Eur Arch Psychiatry Clin Neurosci*, 244: 113-114, 1994.
Gerra et al., "Flumazenil Effects on Growth Hormone Response to Gamma-Hydroxybutyric Acid," *Internat. Clin. Psychopharm.*, 9: 211-215, 1994.
Gessa et al., "Gamma-Hydroxybutyric Acid in the Treatment of Alcohol Dependence," *Clin. Neuropharm.—Supplement*, 15 (Suppl. 1, Pt. A): 303A-304A, 1992.
Gonzalez et al., "Drug Metabolism," in *Goodman & Gilman's The Pharmacological Basis of Therapeutics* (11th ed.), Brunton et al. (eds.), New York: McGraw-Hill. pp. 71-91, 2006.
Halestrap et al., "The *SLC16* Gene Family—From Monocarboxylate Transporters (MCTs) to Aromatic Amino Acid Transporters and Beyond," *Pflugers Arch.*, 447 (5): 619-628, 2004.
Hasan et al., "Pharmacokinetics of Diclofenac Sodium in Normal Man," *Pakistan Jour. Pharmaceutical Sciences*, 18(1): 18-24, 2005.
Hasenbos et al., "Anaesthesia for bullectomy," *Anaesthesia*, 40: 977-980, 1985.
Hechler et al., "Extracellular Events Induced by γ-Hydroxybutyrate in Striatum: A Microdialysis Study," *J. Neurochem.*, 56 (3): 938-944, 1991.
Henry, Thomas R., "The History of Divalproex in Clinical Neuroscience," *Psychopharmacology Bulletin*, 37 (Suppl 2): 5-16, 2003.
Jazz Pharmaceuticals, Inc., "Annex I Summary of Product Characteristics," XYREM® SmPC European Package Insert available at: http://www.ema.europa.eu/docs/en_GB/document_library/EPAR_Product_Information/human/000593/WC500057103.pdf (downloaded May 3, 2013).
Jazz Pharmaceuticals, Inc., "XYREM® (sodium oxybate) oral solution Prescribing Information," XYREM® US Package Insert available at http://www.xyrem.com/xyrem-pi.pdf (downloaded May 3, 2013).
Kuriyama et al., "Blood—Brain Barrier to $H^3$ -γ-Aminobutyric Acid in Normal and Amino Oxyacetic Acid-Treated Animals," *Neuropharmacology*, 10: 103-108, 1971.
Laborit, H., "Gamma-Hydroxybutyrate, Succinic Semialdehyde and Sleep," Laboratoire d'Eutonologie, Hopital Boucicaut, Paris 15, France, pp. 257-274, 1973.
Ladinsky et al., Mode of Action of Gamma-Butyrolactone on the Central Cholinergic System, *Naunyn-Schiniedeberg's Arch. Pharmacal.*, 322: 42-48, 1983.

Lammers et al., "Gammahydroxybutyrate and Narcolepsy: A Double-Blind Placebo-Controlled Study," *Sleep*, 16(3); 216-220, 1993.
Lapierre et al., "The Effect of Gamma-Hydroxybutyrate: A Double-Blind Study of Normal Subjects," *Sleep Research*, 17: 99, 1988 (abstract).
Lapierre et al., "The Effect of Gamma-Hydroxybutyrate on Nocturnal and Diurnal Sleep of Normal Subjects: Further Considerations on REM Sleep-Triggering Mechanisms," *Sleep*, 13(1): 24-30, 1990.
Lee, C.R., "Evidence for the β-Oxidation of Orally Administered 4-Hydroxybutyrate in Humans," *Biochem. Med.*, 17, 284-291: 1977.
Lettieri et al., "Improved Pharmacological Activity via Pro-Drug Modification: Comparative Pharmacokinetics of Sodium γ-Hydroxybutyrate and γ-Butyrolactone," *Research Communications In Chemical Pathology and Pharmacology*, 22(1): 107-118, 1978.
Maitre et al., "A Specific γ-Hydroxybutyrate Receptor Ligand Possesses both Antagonistic and Anticonvulsant Properties," *J. Pharmacol. Exp. Ther.*, 255 (2): 657-663, 1990.
Maitre et al., "Mécanismes d'action d'un medicament détourne: le γ-hydroxybutyrate" ('A mechanism for gamma-hydroxybutyrate (GHB) as a drug and a substance of abuse') (in French), *Med Sci* (Paris), 21 (3): 284-9, 2005.
Mamelak et al., "Sleep-Inducing Effects of Gammahydroxybutyrate," *The Lancet*, 302 (7824): 328-329, 1973.
Mamelak et al., "The Effects of γ-Hydroxybutyrate on Sleep," *Biol. Psychiatry*, 12(2): 273-288, 1977.
Mamelak et al., "Narcolepsy: A Family Study," *Biological Psychiatry*, 14: 821-834, 1979.
Mamelak et al., "Treatment of Narcolepsy and Sleep Apnea with Gammahydroxybutyrate: A Clinical and Polysomnographic Case Study," *Sleep*, 4(1): 105-111, 1981.
Mamelak, "Gammahydroxybutyrate: An Endogenous Regulator of Energy Metabolism," *Neuroscience and Biobehav. Reviews*, 13: 187-198, 1989.
Modi et al., "Dapoxetine has no Pharmacokinetic or Cognitive Interactions with Ethanol in Healthy Male Volunteers," *J. Clin. Pharmac.*, 47(3): 315-322, 2007.
Nema et al., "Excipients and Their Use in Injectable Products," *PDA J. Pharm. Sci. Technol.*, 51(4): 166-171, 1997.
Palatini et al., "Dose-Dependent Absorption and Elimination of Gamma-Hydroxybutyric Acid in Healthy Volunteers," *Eur. J. Clin. Pharmacol.*, 45: 353-356, 1993.
Rapeport et al., "Absence of a Sertraline-Mediated Effect on Digoxin Pharmacokinetics and Electrocardiographic Findings," *J. Clin. Psychiatry*, 57: 16-19, 1996.
Rapeport et al., "Absence of a Sertraline-Mediated Effect on the Pharmacokinetics and Pharmacodynamics of Carbamazepine," *J. Clin. Psychiatry*, 57: 20-23, 1996.
Rapeport et al., "Absence of Effect of Sertraline on the Pharmacokinetics and Pharmacodynamics of Phenytoin," *J. Clin. Psychiatry*, 57: 24-28, 1996.
Rosenberg, G., "The Mechanisms of Action of Valproate in Neuropsychiatric Disorders: Can We See the Forest for the Trees?" *Cel. Mol. Life Sci.*, 64 (16): 2090-2103, 2007.
Roth et al., "γ-Butyrolactone and γ-Hydroxybutyric Acid—I Distribution and Metabolism," *Biochemical Pharmacology*, 15: 1333-1348, 1966.
Roth et al., "γ-Butyrolactone and γ-Hydroxybutyric Acid—II the Pharmacologically Active Form," *Int. J. Neropharmacol.*, 5: 421-428, 1966.
Scharf et al., "The Effects and Effectiveness of γ-Hydroxybutyrate in Patients with Narcolepsy," *J. Clin. Psychiatry*, 46(6): 222-225, 1985.
Scrima et al., "Gamma-Hydroxybutyrate Effects on Cataplexy and Sleep Attacks in Narcoleptics," *Sleep Res.*, 16: 134, 1987, Abstract.
Scrima et al., "Efficacy of Gamma-Hydroxybutyrate versus Placebo in Treating Narcolepsy—Cataplexy: Double-Blind Subjective Measured," *Biol. Psychiatry*, 26: 331-343, 1989.
Scrima et al., "The Effects of γ-Hydroxybutyrate on the Sleep of Narcolepsy Patients: A Double-Blind Study," *Sleep*, 13(6): 479-490, 1990.

(56) References Cited

OTHER PUBLICATIONS

Sériés et al., "Effects of Enhancing Slow-Wave Sleep by Gamma-Hydroxybutyrate on Obstructive Sleep Apnea," *Am. Rev. Respir. Dis.*, 1378-1383, 1992.

Smolders et al., "Tonic GABA-ergic Modulation of Striatal Dopamine Release Studied by In Vivo Microdialysis in the Freely Moving Rat," *Eur. J. Pharmacol.*, 284 (1-2): 83-91, 1995.

Strong, "γ-Hydroxybutyric Acid and Intracranial Pressure," *The Lancet*, vol. 1: No. 8389, 1984.

Van Den Bogert et al., "Placentatransfer of 4-Hydroxybutyric Acid in Man," *Anesthesiology and Intensive Care Medicine*, 110: 55-64, 1978.

Vickers, M.D., "Gammahydroxybutyric Acid," *Int. Anesth. Clinic*, 7: 75-89, 1969.

Waszkielewicz et al., "γ-Hydrobutyric Acid (GHB) and its Chemical Modifications: A Review of the GHBergic System," *Pol J Pharmacol.*, 56 (1): 43-49, 2004.

Wesnes et al., "Moxonidine and Cognitive Function: Interactions with Moclobemide and Lorazepam," *Eur. J. Clinic. Pharmacol.*, 52: 351-358, 1997.

Wesnes et al., "The Memory Enhancing Effects of a Ginkgo biloba/Panax ginseng Combination in Healthy Middle-Aged Volunteers," *Psychopharmacology*, 152: 353-361, 2000.

Williams et al., "Absence of Effect of Sertraline on Time-Based Sensitization of Cognitive Impairment with Haloperidol," *J. Clinic. Psych.*, 57 ,7-11, 1996.

Wu et al., "γ-Hydroxybutyric acid (GHB) and γ-aminobutyric acid$_B$ receptor (GABA$_B$ R) binding sites are distinctive from one another: molecular evidence," *Neuropharmacology*, 47 (8): 1146-56, 2004.

Yamada et al., "Effect of Butyrolactone and Gamma-Hydroxybutyrate on the EEG and Sleep Cycle in Man," *Electroenceph. Clin. Neurophysiol.*, 22: 558-562, 1967.

United States Patent and Trademark Office, Notice of Allowance and Fee(s) Due mailed Dec. 19, 2013, in related U.S Appl. No. 13/872,997.

Wellendorph et al., "Phenylacetic acids and the structurally related non-steroidal anti-inflammatory drug diclofenac bind to specific c-hydroxybutyric acid sites in rat brain," *Fundamental & Clinical Pharmacology*, 23: 207-213, 2009.

Orphan Medical, Inc., NDA 21196, Major Amendment, filed Mar. 26. 2001, "Review and Evaluation of Clinical Data." http://www.fda.gov/ohrms/dockets/ac/01/briefing/3754b1_02_section%204.PDF (as downloaded on Mar. 4, 2004).

PCT, International Search Report, mailed Jun. 24, 2014, in International Patent Application No. PCT/US2014/019217.

PCT. Written Opinion, mailed Jun. 24. 2014, in International Patent Application No. PCT/US2014/019217.

Fuller et al., "From Club Drug to Orphan Drug: Sodium Oxybate (Xyrem) for the Treatment of Cataplexy," *Pharmacotherapy*, 23(9): 1205-1209, 2003.

Hechler et al., "y-Hydroxybutyrate Conversion into GABA Induces Displacement of GABA$_B$ Binding that is Blocked by Valproate and Ethosuximide," *The Journal of Pharmacology and Experimental Therapeutics*, 281(2): 753-760, 1997.

Bhattacharya et al., "GHB (y-Hydroxybutyrate) Carrier-Mediated Transport across the Blood-Brain Barrier," *The Journal of Pharmacology and Experimental Therapeutics*, 311(1): 92-98, 2004.

\* cited by examiner

METHOD OF ADMINISTRATION OF GAMMA HYDROXYBUTYRATE WITH MONOCARBOXYLATE TRANSPORTERS

This application is a continuation application of U.S. patent application Ser. No. 13/837,714, filed Mar. 15, 2013, which claims the benefit of U.S. Provisional Application No. 61/771,557, filed Mar. 1, 2013, and U.S. Provisional Application No. 61/777,873, filed Mar. 12, 2013, all of which applications are hereby incorporated by reference in their entireties.

BACKGROUND

This application relates to methods for safely administering gamma hydroxybutyrate (GHB) together with one or more other monocarboxylate transporter (MCT) inhibitors for therapeutic purposes. Example transporter inhibitors are valproate, diclofenac, and ibuprofen and combinations thereof.

SUMMARY OF THE INVENTION

One embodiment of the present invention is a method for treating a patient who is suffering from excessive daytime sleepiness, cataplexy, sleep paralysis, apnea, narcolepsy sleep time disturbances, hypnagogic hallucinations, sleep arousal, insomnia, and nocturnal myoclonus with gamma-hydroxybutyrate (GHB) or a salt thereof, comprising: orally administering to the patient in need of treatment, an adjusted dosage amount of the salt of GHB when the patient is receiving a concomitant administration of valproate. In certain embodiments, the adjusted amount is reduced at least about 1%, 5%, 10%, 15%, 20%, 25%, 30%, 35%, 40%, 45%, or 50% of the normal dose of the salt of GHB normally given to the patient. In certain embodiments, the amount of GHB is reduced at least about 10% and about 30% of the normal administration and the daily administration of the GHB salt is between 1 gram and 10 grams. In certain embodiments, the adjusted amount is reduced between the ranges of about 1% to 5%, about 5% to 10%, about 10% to 15%, about 15% to 20%, about 20% to 25%, about 25% to 30%, about 30% to 35%, about 35% to 40%, about 40% to 45%, or about 45% or 50%, relative to the normal dose of the salt of GHB normally given to the patient. In certain embodiments, the adjusted amount is reduced between the range of about 1% to 50%, about 1% to 45%, about 1% to 40%, about 1% to 35%, about 1% to 30%, about 1% to 25%, about 1% to 20%, about 1% to 15%, about 1% to 10%, about 1% to 5%, about 5% to 50%, about 5% to 45%, about 5% to 40%, about 5% to 35%, about 5% to 30%, about 5% to 25%, about 5% to 20%, about 5% to 15%, about 5% to 10%, about 10% to 50%, about 10% to 45%, about 10% to 40%, about 10% to 35%, about 10% to 30%, about 10% to 25%, about 10% to 20%, about 10% to 15%, about 15% to 50%, about 15% to 45%, about 15% to 40%, about 15% to 35%, about 15% to 30%, about 15% to 25%, about 15% to 20%, about 15% to 15%, about 15% to 10%, about 20% to 50%, about 20% to 45%, about 20% to 40%, about 20% to 35%, about 20% to 30%, about 20% to 25%, about 25% to 50%, about 25% to 45%, about 25% to 40%, about 25% to 35%, about 25% to 30%, about 30% to 50%, about 30% to 45%, about 30% to 40%, about 30% to 35%, about 35% to 50%, about 35% to 45%, about 35% to 40%, about 40% to 50%, relative to the normal dose of the salt of GHB normally given to the patient.

Another embodiment of the invention is a method of safely administering GHB a salt thereof for excessive daytime sleepiness, cataplexy, sleep paralysis, apnea, narcolepsy, sleep time disturbances, hypnagogic hallucinations, sleep arousal, insomnia, and nocturnal myoclonus in a human patient, comprising: determining if the patient is has taken, or will take a concomitant dose of valproate; orally administering a reduced amount of the GHB or GHB salt to the patient compared to the normal dose so as to diminish the additive effects of the GHB or GHB salt when administered with valproate. The amount of GHB is reduced at least 10% to 30%, or at least+ 15% of the normal administration.

One embodiment of the present invention is a method for treating a patient who is suffering from excessive daytime sleepiness, cataplexy, sleep paralysis, apnea, narcolepsy sleep time disturbances, hypnagogic hallucinations, sleep arousal, insomnia, and nocturnal myoclonus with GHB or a salt thereof, comprising: orally administering to the patient in need of treatment, an adjusted dosage amount of the salt of GHB when the patient is receiving a concomitant administration of diclofenac. In certain embodiments, the adjusted amount is at least about 1%, 5%, 10%, 15%, 20%, 25%, 30%, 35%, 40%, 45%, or 50% higher than the normal dose of the salt of GHB normally given to the patient. In certain embodiments, the increased amount of GHB is at least about 15% more than the normal administration and the daily administration of the GHB salt is between 1 gram and 10 grams. In certain embodiments, the adjusted amount is increased between the range of about 1% to 5%, about 5% to 10%, about 10% to 15%, about 15% to 20%, about 20% to 25%, about 25% to 30%, about 30% to 35%, about 35% to 40%, about 40% to 45%, or about 45% or 50%, relative to the normal dose of the salt of GHB normally given to the patient. In certain embodiments, the adjusted amount is increased between the range of about 1% to 50%, about 1% to 45%, about 1% to 40%, about 1% to 35%, about 1% to 30%, about 1% to 25%, about 1% to 20%, about 1% to 15%, about 1% to 10%, about 1% to 5%, about 5% to 50%, about 5% to 45%, about 5% to 40%, about 5% to 35%, about 5% to 30%, about 5% to 25%, about 5% to 20%, about 5% to 15%, about 5% to 10%, about 10% to 50%, about 10% to 45%, about 10% to 40%, about 10% to 35%, about 10% to 30%, about 10% to 25%, about 10% to 20%, about 10% to 15%, about 15% to 50%, about 15% to 45%, about 15% to 40%, about 15% to 35%, about 15% to 30%, about 15% to 25%, about 15% to 20%, about 15% to 15%, about 15% to 10%, about 20% to 50%, about 20% to 45%, about 20% to 40%, about 20% to 35%, about 20% to 30%, about 20% to 25%, about 25% to 50%, about 25% to 45%, about 25% to 40%, about 25% to 35%, about 25% to 30%, about 30% to 50%, about 30% to 45%, about 30% to 40%, about 30% to 35%, about 35% to 50%, about 35% to 45%, about 35% to 40%, about 40% to 50%, relative to the normal dose of the salt of GHB normally given to the patient. See the product insert for normal dose ranges of GHB as sold by Jazz Pharmaceuticals. GHB is commercially known as Xyrem®.

In another embodiment, the invention is a method of safely administering a GHB salt for excessive daytime sleepiness, cataplexy, sleep paralysis, apnea, narcolepsy, sleep time disturbances, hypnagogic hallucinations, sleep arousal, insomnia, and nocturnal myoclonus in a human patient, comprising: determining if the patient has taken, or will take a concomitant dose of diclofenac; orally administering an increased amount of a GHB salt to the patient so as to compensate for the effects of diclofenac on the GHB salt when concomitantly administered.

Another embodiment of the present invention is a method for treating a patient who is suffering from narcolepsy wherein said patient is currently taking or has been prescribed GHB or a salt thereof, comprising determining if the patient is taking or has also been prescribed valproate or diclofenac; and adjusting the dose of the GHB or GHB salt to compensate for the effect caused by valproate or diclofenac. In certain embodiments, the method additionally comprises administering the adjusted dose to the patient.

Another embodiment of the present invention is a method for treating a patient who is suffering from excessive daytime sleepiness, cataplexy, sleep paralysis, apnea, narcolepsy, sleep time disturbances, hypnagogic hallucinations, sleep arousal, insomnia, and nocturnal myoclonus with a salt of gamma GHB, wherein said patient is also being treated with valproate or diclofenac, comprising: administering to the patient a daily dose of a GHB salt wherein said daily dose is administered at an amount sufficient to reduce or eliminate additive effects.

The embodiments of the present invention can administer the GHB at a level of between 1 and 4.5 grams/day or between 6 and 10 grams/day. The concentration of the formulation can be between 350-750 mg/ml or 450-550 mg/ml and a pH between 6-10 or 6.5-8.

Another embodiment of the present invention is a method for treating a patient who is suffering from narcolepsy, comprising: administering a salt of GHB or a salt thereof to a patient or determining whether the patient is currently on a GHB drug regimen; determining if the patient is also being administered ibuprofen; and advising a patient to cease or ceasing the administration of ibuprofen. In some embodiments, patients benefitting from this directive when the patient has will have a renal impairment.

Another embodiment of the present invention is a method for treating a patient who is suffering from narcolepsy, comprising: administering a therapeutically effective amount of a formulation containing GHB or a salt thereof to a patient at a concentration of between 450 and 550 mg/ml and a pH between 6 and 8, said formulation being administered before bed and 1-2 hours thereafter; determining if the patient is also being administered valproate; warning of a potential drug/drug interaction due to the combination of valproate and GHB; and reducing the dose of the GHB or GHB salt at least 15% to compensate for the effect caused by valproate. Another embodiment of the present invention is a method for treating a patient who is suffering from narcolepsy, comprising: administering a therapeutically effective amount of a formulation containing GHB or a salt thereof to a patient at a concentration of between 450 and 550 mg/ml and a pH between 6 and 8, said formulation being administered before bed and 1-2 hours thereafter; determining if the patient is also being administered diclofenac; warning of a potential drug/drug interaction due to the combination of diclofenac and the GHB salt; and increasing the dose of the GHB salt at least 15% to compensate for the effect caused by diclofenac.

In each of the embodiments of the invention the method includes administering GHB at between 1 and 4.5 grams/day or between 6 and 10 grams/day and at a concentration of between 350-750 or 450-550 mg/ml, and a pH between 6-10 or between 6.5-8. In further embodiments the valproate or diclofenac is administered within three days, one or two weeks (before or after) of GHB administration. In another embodiment, the present invention is a method wherein aspirin is also administered to the patient, especially with valproate.

In a further embodiment the method can include administering GHB as a single salt or a mixture of salts of GHB selected from the group consisting of a sodium salt of hydroxybutyrate (Na.GHB), a potassium salt of gamma-hydroxybutyrate (K.GHB), a magnesium salt of gamma-hydroxybutyrate (Mg.(GHB)$_2$), and a calcium salt of gamma-hydroxybutyrate (Ca.(GHB)$_2$).

In a further embodiment the method can include administering GHB to a patient suffering from excessive daytime sleepiness, comprising: administering a therapeutically effective amount of GHB to the patient; determining if the patient has concomitant administration of an MCT inhibitor; and adjusting the GHB dose or ceasing administering of the MCT inhibitor to maintain the effect of the GHB.

In any of the versions of the invention, the methods optionally further include administering aspirin to the patient.

In a further embodiment the method of administering GHB to a patient in need thereof comprises administering to the patient a therapeutically effective amount of GHB while avoiding concomitant of a diclofenac or valproate.

Another embodiment of the invention comprises a method of administering GHB or a salt thereof (GHB) to a patient with narcolepsy, wherein said patient is also in need of diclofenac, comprising administering to the patient a daily dosage of between 6 g and 10 g GHB or a GHB salt per day while avoiding diclofenac concomitant administration, and any one or more of the following: (a) advising the patient that diclofenac should be avoided or discontinued, (b) advising the patient that concomitant administration of GHB with drugs that are MCT inhibitors can alter the therapeutic effect or adverse reaction profile of GHB, (c) advising the patient that concomitant administration of GHB with diclofenac can alter the therapeutic effect or adverse reaction profile of GHB, (d) advising the patient that use of GHB in patients being treated with diclofenac is contraindicated, (e) advising the patient that concomitant administration of GHB and diclofenac resulted in an decrease in exposure to GHB, or (f) advising the patient MCT inhibitors should be used with caution in patients receiving GHB due to the potential for increased GHB clearance.

Another embodiment of the invention comprises a administering GHB to a patient with narcolepsy, wherein said patient is also in need of valproate, comprising administering to the patient a daily dosage of between 6 g and 10 g GHB per day while avoiding valproate concomitant administration, and any one or more of the following: (a) advising the patient that valproate should be avoided or discontinued, (b) advising the patient that concomitant administration of GHB with drugs that are MCT inhibitors can alter the therapeutic effect or adverse reaction profile of GHB, (c) advising the patient that concomitant administration of GHB with valproate can alter the therapeutic effect or adverse reaction profile of GHB, (d) advising the patient that use of GHB in patients being treated with valproate is contraindicated, (e) advising the patient that concomitant administration of GHB and valproate resulted in an increase in exposure to GHB, or (f) advising the patient that MCT inhibitors should be used with caution in patients receiving GHB due to the potential for increased GHB clearance.

In another embodiment, the present invention is a method for distributing a drug containing GHB or a salt thereof to an approved pharmacy, the method comprising: identifying an approved pharmacy that has an established management system to dispense information concerning the risks associated with ingesting a MCT inhibitor concomitantly to said drug to patients that are prescribed said drug; providing said pharmacy with said information related to the risks; and authorizing distribution of said drug to said pharmacy, wherein said pharmacy dispenses the drug with said information when filling a prescription for said drug. The method may also comprise including an electronic or written alert, which can explain the risks, to employees to dispense said information with said drug when prescriptions are filled. Also, the information can be dispensed when a subject refills said prescription. The warnings would be as recited above.

The methods of the present invention may include a warning for patients not to operate hazardous machinery, including automobiles or airplanes, until they are reasonably certain that GHB does not affect them adversely and not to engage in hazardous occupations or activities requiring complete mental alertness or motor coordination, such as operating machinery or a motor vehicle or flying an airplane, for at least 6, 7, 8 or 9 hours after taking the second nightly dose of GHB. Any information dispensed with said drug advises patients of the potential for enhanced potency of said drug if said patients also take valproate or advises patients of the potential for decreased potency of said drug if said patients also take diclofenac.

Another embodiment of the present invention is a method of administering GHB to a patient in need thereof, comprising administering to the patient a therapeutically effective amount of GHB while avoiding concomitant administration of diclofenac or valproate.

The invention may also comprise a method for reducing the effects of GHB toxicity in a patient in need thereof, comprising administering to said patient an effective amount of diclofenac such that the toxic effects of GHB are reduced. It may also comprise a method for potentiating the beneficial effects of GHB in a patient in need thereof comprising concomitantly administering to said patient an effective amount of valproate such that the beneficial effects of GHB are increased.

DETAILED DESCRIPTION OF THE INVENTION

Figure 1:
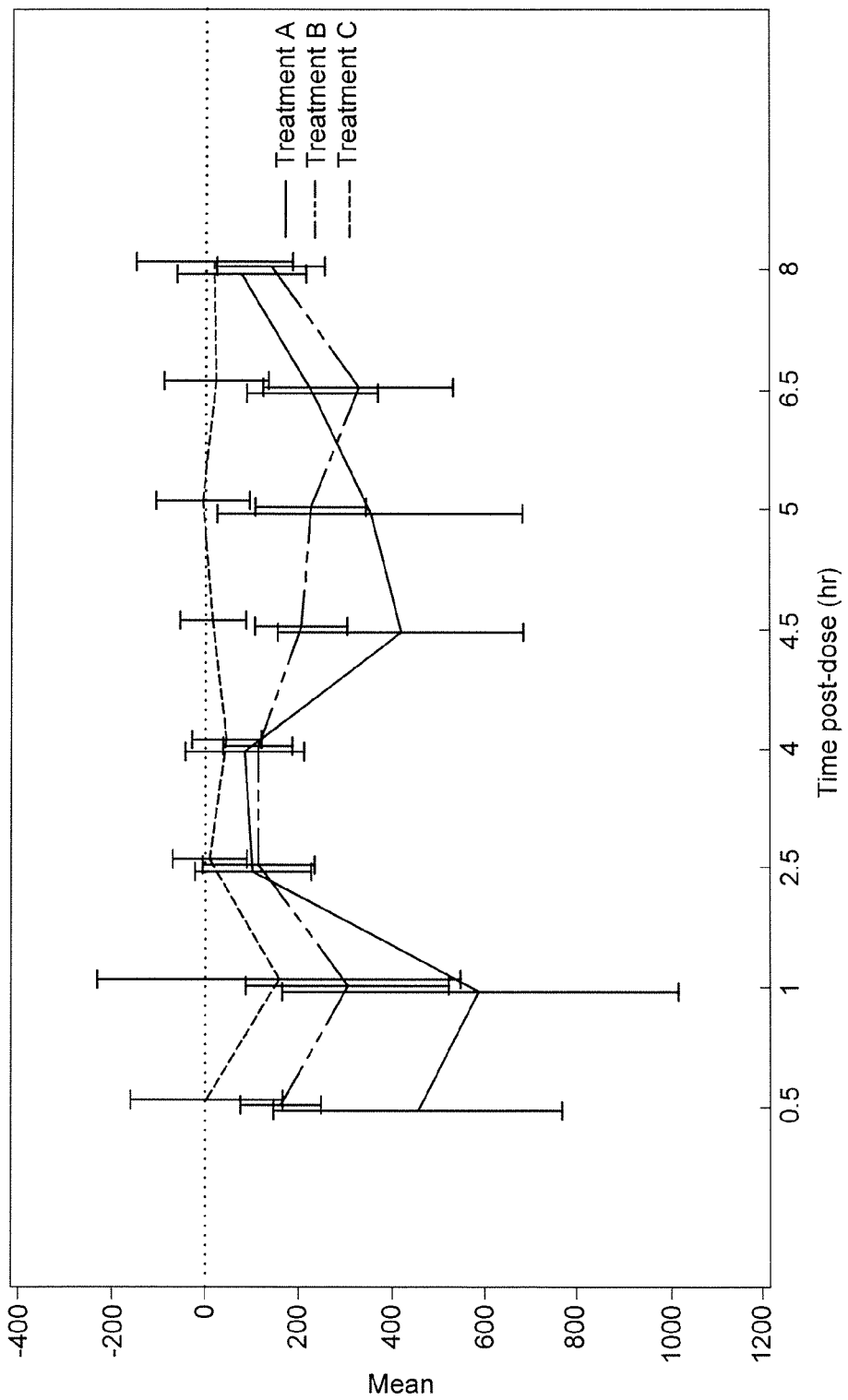
FIG. 1 shows change from baseline figure (LSmean with 95% CI) for Power of Attention (ms) (PD Completer Population). Treatment A=diclofenac placebo+Xyrem®. Treatment B=diclofenac+Xyrem®. Treatment C=diclofenac+Xyrem® placebo.

The following patents and applications are hereby incorporated by reference in their entireties for all purposes: U.S. Pat. Nos. 6,472,431, 6,780,889, 7,262,219, 7,851,506, 8,263,650, 8,324,275; 7,895,059; 7,797,171; 7,668,730; 7,765,106; 7,765,107; 61/317,212, Ser. Nos. 13/071,369, 13/739,886, 12/264,709, PCT/US2010/033572, PCT/US2009/061312, 2009/0137565; and 2012/0076865. The following patents are also incorporated by reference: U.S. Pat. No. 5,380,937; U.S. Pat. No. 4,393,236 German Patent DD 237,309 A1; and British Pat. No. 922,029.

Objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

The following references, to the extent that they provide exemplary procedural or other details supplementary to those set forth herein, are specifically incorporated herein by reference.

Arena and Fung, "Absorption of sodium .gamma.-hydroxybutyrate and its prodrug .gamma.-butyrolactone: relationship between in vitro transport and in vivo absorption," J. Pharmaceutical Sciences, 69(3):356-358, 1980.

Bedard, Montplaisir, Godbout, Lapierre, "Nocturnal .gamma.-Hydroxybutyrate—Effect on Periodic Leg Movements and Sleep Organization of Narcoleptic Patients," 12(1):29-36, 1989.

Broughton and Mamelak, "The treatment of narcolepsy-cataplexy with nocturnal gamma-hydroxybutyrate," Le Journal Canadien Des Sciences Neurologiques. 6(1):1-6, 1979.

Ferrara, Zotti, Tedeschi, Frison, Castagna. Gessa and Gallimberti, "Gamma-hydroxybutyric acid in the treatment of alcohol dependent," Clin. Neuropharm., 15(1, PtA):303A-304A, 1992.

Gessa, Diana, Fadda, Colombo, "Gamma-hydroxybutyric acid (GHB) for treatment of ethanol dependence," Clin. Neuropharm.—Supplement, 1992. Gessa et al., Clin. Neuropharm., 15(supp.):303A-304A, 1992

Gessa et al., Internat. Clin. Psychopharm., 1994.

Hasenbos and Gieien, "Anaesthesia for bullectomy," Anaesthesia, 40:977-980, 1985.

Laborit, "Gamma-Hydroxybutyrate, Succinic Semi aldehyde and Sleep," Laboratojre d'Eutonologie, Hopital Boucicaut, Paris 15, France, 1973.

Ladinsky. Consolo, Zatta, Vezzani. Mode of Action of Gamma-Butyrolactone on the Central Cholinergic System, Naunyn-Schmiedeberg's Arch. Pharmacal., 322:42-48, 1983.

Lammers et al., "Gammahydroxybutyrate and narcolepsy: a double-blind placebo-controlled study," Sleep, 16(3); 216-220, 1993.

Lapierre, Montplaisir, Lamarre, Bedard, "The Effect of Gamma-Hydroxybutyrate on Nocturnal and Diurnal Sleep of Normal Subjects: Further Considerations on REM Sleep-Triggering Mechanisms," Sleep. 13(1):24-30, 1990.

Lapierre et al., "Increases in delta sleep," 1988. Lapierre et al., "Increases in delta sleep," 1990. Lee, C. R. "Evidence for the .beta.-Oxidation of Orally Administered 4-Hydroxybutyrate in Humans" Biochem. Medicine 17, 284-291, 1977.

Lettieri and Fung, "Improved pharmacological activity via pro-drug modification: comparative pharmacokinetics of sodium .gamma.-hydroxybutyrate and .gamma.-butyrolactone," Research Communications In Chemical Pathology and Pharmacology. 22(1):107-118. 1978.

Mamelak, 1977; "Effects Of Gamma Hydroxybutyrate On Sleep," Biol. Psychiatry 12, 273-288. Mamelak, "Gamma-hydroxybutyrate (GHB): An endogenous regulator of energy metabolism," Neuroscience and Biobehay. Reviews, 13: 189-198, 1989.

Mamelak, "Gammahydroxybutyrate: An Endogenous Regulator of Energy Metabolism," Neuro. & Biobehay. Rev., 13 187-198, 1989.

Mamelak, 1979; Mamelak, Escriu, Stokan "The effects of gamma-hydroxybutyrate on sleep," Biol. Psychiatry, 12(2):273-288. 1977.

Mamelak, Escriu, Stokan, "Sleep-Inducing Effects of Gammahydroxybutyrate," The Lance, p. 328-329. 1973.

Nema, et al., "Excipients and their use in injectable products," PDA J. Plarm. Sci. Technol., 51(4):166-171, 1997.

Palatini, Tedeschi, Frison, Padrini, Zordan, Orlando, Gallimberti, Gessa, Ferrara, "Dose dependent absorption and elimination of gamma-hydroxybutyric acid in healthy volunteers," Eur. J. Clin. Pharmacol., 45:353-356, 1993.

Roth and Giarman, ".gamma.-Butyrolactone and .gamma.-Hydroxybutyric Acid-I, Distribution and Metabolism," Biochemical Pharmacology, 15:1333-1348, 1966.

Scharf, Brown, Woods, Brown, Hirschowitz, "The effects and effectiveness of gammahydroxybutyrate In patients with narcolepsy," J. Clin. Psychiatry, 46(6)222-225, 1985.

Scrima, Hartman, Johnson, Thomas, Hiller, "Efficacy of gamma-hydroxybutyrate versus placebo in treating narcolepsy-cataplexy: Double-blind subjective measured," Biol. Psychiatry, 26:331-343, 1989.

Scrima, Hartman, Johnson, Thomas, Hiller, "The Effects of .gamma.-Hydroxybutyrate on the Sleep of Narcolepsy Patients: A Double-Blind Study," Sleep, 13(6):479-490, 1990.

Scrima, et al, "Sleep Res. 16, 134, 1987, Abstract. Series, Series, Cormier, "Effects of Enhancing Slow-Wave Sleep by Gamma-Hydroxybutyrate on Obstructive Sleep Apnea," Am. Rev. Respir. Dis., 1378-1383, 1992.

Strong, ".gamma.-Hydroxybutyric acid and Intracranial Pressure," The Lancet, Vol. 1: No. 8389, 1984. van den Bogert, Vree, van der Kleijn, Damsma, "Placentatransfer of 4-Hydroxybutyric Acid in Man."

Vickers, "Gammahydroxybutyric Acid," Int. Anesth. Clinic, 7:75.89, 1969.

Lee, Biochem. Med. 17:234-291, 1977. Yamada, Yamamoto, Fujiki, Hishikawa, Kaneko, "Effect of Butyrolactone and Gamma-Hydroxybutyrate on the EEG and Sleep Cycle in Man," Electroenceph. Clin. Neurophysiol., 22:558-562, 1967.

Yamada et al., 1967. Wu, Ying; Ali, Saima; Ahmadian, Gholamreza; Liu, Chun Che; Wang, Yu Tian; Gibson, K. Michael; Calver, Andrew R.; Francis, Joseph et al. (2004). "Gamma-hydroxybutyric acid (GHB) and gamma-aminobutyric acidB receptor (GABABR) binding sites are distinctive from one another: molecular evidence". Neuropharmacology 47 (8): 1146-56.

Cash, C; Gobaille, S; Kemmel, V; Andriamampandry, C; Maitre, M (1999). "γ-hydroxybutyrate receptor function studied by the modulation of nitric oxide synthase activity in rat frontal cortex punches". Biochemical Pharmacology 58 (11): 1815-9.

Maitre M, Humbert J P, Kemmel V, Aunis D, Andriamampandry C (2005). "A mechanism for gamma-hydroxybutyrate (GHB) as a drug and a substance of abuse" (in French). Med Sci (Paris) 21 (3): 284-9. Waszkielewicz A, Bojarski J (2004). "Gamma-hydrobutyric acid (GHB) and its chemical modifications: a review of the GHBergic system" (PDF). Pol J Pharmacol 56 (1): 43-9.

Kuriyama K, Sze P Y (1971). "Blood-brain barrier to H3-gamma-aminobutyric acid in normal and amino oxyacetic acid-treated animals". Neuropharmacology 10 (1): 103-8.

Dimitrijevic N, Dzitoyeva S, Satta R, Imbesi M, Yildiz S, Manev H (2005). "*Drosophila* GABA(B) receptors are involved in behavioral effects of gamma-hydroxybutyric acid (GHB)". Eur. J. Pharmacol. 519 (3): 246-52.

Banerjee P K, Snead O C (1995). "Presynaptic gamma-hydroxybutyric acid (GHB) and gamma-aminobutyric acidB (GABAB) receptor-mediated release of GABA and glutamate (GLU) in rat thalamic ventrobasal nucleus (VB): a possible mechanism for the generation of absence-like seizures induced by GHB". J. Pharmacol. Exp. Ther. 273 (3): 1534-43.

Hechler V, Gobaille S, Bourguignon J J, Maitre M (1991). "Extracellular events induced by gamma-hydroxybutyrate in striatum: a microdialysis study". J. Neurochem. 56 (3): 938-44. Maitre, M; Hechler, V; Vayer, P; Gobaille, S; Cash, C D; Schmitt, M; Bourguignon, J J (1990). "A specific gamma-hydroxybutyrate receptor ligand possesses both antagonistic and anticonvulsant properties". J. Pharmacol. Exp. Ther. 255 (2): 657-63.

Smolders I, De Klippel N, Sarre S, Ebinger G, Michotte Y (1995). "Tonic GABAergic modulation of striatal dopamine release studied by in vivo microdialysis in the freely moving rat". Eur. J. Pharmacol. 284 (1-2): 83-91.

In the specification and claims that follow, references will be made to a number of terms which shall be defined to have the following meaning.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

"Concomitant" and "concomitantly" as used herein refer to the administration of at least two drugs to a patient either subsequently, simultaneously, or consequently within a time period during which the effects of the first administered drug are still operative in the patient. Thus, if the first drug is, e.g., Xyrem®, or GHB, and the second drug is valproate, the concomitant administration of the second drug occurs within two weeks, preferably within one week or even three days, before or after the administration of the first drug.

"Dosage amount" means an amount of a drug suitable to be taken during a fixed period, usually during one day (i.e., daily).

"Dosage amount adapted for oral administration" means a dosage amount that is of an amount deemed safe and effective for the particular patient under the conditions specified. As used herein and in the claims, this dosage amount is determined by following the recommendations of the drug manufacturer's Prescribing Information as approved by the US Food and Drug Administration.

"Dosing regimen" means the dose of a drug taken at a first time by a patient and the interval (time or symptomatic) and dosage amounts at which any subsequent doses of the drug are taken by the patient. Each dose may be of the same or a different dosage amount.

A "dose" means the measured quantity of a drug to be taken at one time by a patient.

A "patient" means a human in need of medical treatment. In one embodiment medical treatment can include treatment of an existing condition, such as a disease or disorder, prophylactic or preventative treatment, or diagnostic treatment. In another embodiment, medical treatment also includes administration to treat excessive daytime sleepiness, cataplexy, sleep paralysis, apnea, narcolepsy, sleep time disturbances, hypnagogic hallucinations, sleep arousal, insomnia, and nocturnal myoclonus.

"Providing" means giving, administering, selling, distributing, transferring (for profit or not), manufacturing, compounding, or dispensing.

The terms "therapeutically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, an improvement in clinical condition, or reduction in symptoms. The precise effective amount for a subject will depend upon the subject's body weight, size, and health; the nature and extent of the condition; and the therapeutic or combination of therapeutics selected for administration. Where a drug has been approved by the U.S. Food and Drug Administration (FDA), a "therapeutically effective amount" refers to the dosage approved by the FDA or its counterpart foreign agency for treatment of the identified disease or condition.

"Side effect" means a secondary effect resulting from taking a drug. The secondary effect can be a negative (unfavorable) effect (i.e., an adverse side effect) or a positive (favorable) effect.

Pharmacokinetic parameters referred to herein describe the in vivo characteristics of drug (or a metabolite or a surrogate marker for the drug) over time. These include plasma concentration (C), as well as $C_{max}$, $C_n$, $C_{24}$, $T_{max}$, and AUC. The term "$T_{max}$" refers to the time from drug administration until $C_{max}$ is reached. "AUC" is the area under the curve of a graph of the measured plasma concentration of an active agent vs. time, measured from one time point to another time point. For example $AUC_{0-t}$ is the area under the curve of plasma concentration versus time from time 0 to time t, where time 0 is the time of initial administration of the drug. Time t can be the last time point with measurable plasma concentration for an individual formulation. The $AUC_{0-infin.}$ or $AUC_{0-INF}$ is the calculated area under the curve of plasma concentration versus time from time 0 to time infinity. In steady-state studies, $AUC_{0-tau}$ is the area under the curve of plasma concentration over the dosing interval (i.e., from time 0 to time .tau. (tau), where tau is the length of the dosing interval.

It may be advantageous to incorporate a pharmacy management system into the method of the present invention. Pharmacy management systems are computer-based systems that are used by commercial pharmacies to manage prescriptions and to provide pharmacy and medical personnel with warnings and guidance regarding drugs being administered to patients. Such systems typically provide alerts warning either or both of health care providers and patients when a drug that may be harmful to the particular patient is prescribed. For example, such systems can provide alerts warning that a patient has an allergy to a prescribed drug, or is receiving concomitant administration of a drug that can have a dangerous interaction with a prescribed drug. U.S. Pat. Nos. 7,895,059; 7,797,171; 7,668,730; 7,765,106; 7,765,107; 5,758,095, 5,833,599, 5,845,255, 6,014,631, 6,067,524, 6,112,182, 6,317,719, 6,356,873, and 7,072,840, each of which is incorporated herein by reference, disclose various pharmacy management systems and aspects thereof. Example pharmacy management systems are now commercially available, e.g., CENTRICITY Pharmacy from BDM Information Systems Ltd., General Electric Healthcare, Waukesha, Wis., Rx30 Pharmacy Systems from Transaction Data Systems, Inc., Ocoee, Fla., SPEED SCRIPT from Digital Simplistics, Inc., Lenexa, Kans., and various pharmacy management systems from OPUS-ISM, Hauppauge, N.Y.

In some embodiments, a pharmacy management system may be required or preferred as part of a drug distribution program. For example, the present invention includes a method for distributing a drug containing GHB or a salt thereof to an approved pharmacy, the method comprising: (1) Identifying an approved pharmacy that has an established management system to dispense information concerning the risks associated with ingesting a MCT inhibitors concomitantly to said drug to patients that are prescribed said drug; (2) Providing said pharmacy with said information related to the risks; and (3) Authorizing distribution of said drug to said pharmacy, wherein said pharmacy dispenses the drug with said information when filling a prescription for said drug. The established management system may include an electronic alert to employees to dispense said information with said drug when prescriptions are filled. Such information may be dispensed in written form, for example in a brochure explaining the risks of concomitant ingestion of GHB and an MCT inhibitor such as diclofenac, valproate, or ibuprofen or combinations thereof. For example, the information dispensed with GHB may advise a patient of the potential for enhanced potency of GHB if the patient also takes valproate. Alternatively, or in addition thereto, the information dispensed with GHB may advise a patient of the potential for decreased potency of GHB if the patient also takes diclofenac. Such information may also be dispensed in verbal form. Distributors may maintain a directory of approved pharmacies, for example in a computer readable storage medium, to further ensure that GHB is dispensed only to patients who are advised of the additive effects.

In addition, the system can prevent the dispensing of GHB or salt thereof until proper testing or confirmation is obtained that the patient is not taking or going to take valproate or diclofenac concomitantly with GHB. Alternatively, the patient can be warned of the adverse effect and instructed to modify the dose of GHB to accommodate the increased or reduced effects of GHB due to valproate or diclofenac.

A pharmacy management system of the present invention can be a REMS system as shown in U.S. Pat. Nos. 7,895,059; 7,797,171; and 7,668,730 and also include monitoring for concomitant use of diclofenac, valproate, or ibuprofen, or combinations thereof. Warnings may be administered through the existing pharmacy management system as described in the patents above.

One embodiment of the present invention, without being limited by theory, is the discovery of drug interactions that change either, or both, the efficacy or safety profile of GHB. The three compounds are valproate, diclofenac, and ibuprofen or combinations thereof. To achieve the above benefits, GHB of the present invention can be administered in a reduced amount when a second compound, such as valproate, is concomitantly administered with GHB. It can also be administered in an increased amount to overcome any effects of diclofenac. The compounds can also be avoided or discontinued to prevent unsafe concomitant administration.

In one embodiment of the present invention, concomitant administration of GHB with other agents is monitored and potential changes to the doses of GHB are made, or changes in the administration of other compounds are made. In one embodiment of the present invention, when GHB was concomitantly administered with ibuprofen, there were pharmacokinetic (PK) changes consistent with monocarboxylic transporter (MCT) inhibition and renal excretion of GHB doubled (statistically significant). Plasma levels were about ~5% lower, which was statistically significant. In another embodiment of the present invention, when GHB and Diclofenac are concomitantly administered, PD effects were significantly reduced. In another embodiment of the present invention, when GHB and divalproate were concomitantly administered, PK showed both MCT and GHB dehydrogenase inhibition, with the latter predominating. MCT inhibition caused renal clearance to be increased 30% (statistically significant). GHB dehydrogenase inhibition caused systemic exposure (plasma AUC) to be increased 26%. Both measures are statistically significant and outside FDA "equivalence window". PD shows more pronounced effects with concomitant administration.

One embodiment is a method of administering a therapeutically effective amount of GHB to a patient in need of treatment, such as with narcolepsy, the invention provides an improvement that comprises avoiding or discontinuing administration of a compound that affects GHB potency and administering a therapeutically effective amount of GHB.

The compound can be diclofenac or valproate and they can alter the therapeutic effect or adverse reaction profile of GHB.

Gamma Hydroxybutyrate (GHB)

GHB (also called oxysorbate or oxybate) is approved in the United States (US) for the treatment of excessive daytime sleepiness (EDS) and for the treatment of cataplexy, both in patients with narcolepsy. GHB is commercially sold as Xyrem® sodium oxybate by Jazz Pharmaceuticals. Sodium oxybate is the sodium salt of the endogenous neurotransmitter gamma hydroxybutyrate (GHB), which is found in many tissues of the body. "GHB", oxybate, a GHB salt or Xyrem® will be used to refer to these active forms. It can be used as a sodium, calcium, potassium, or magnesium salt. See U.S. patent application Ser. No. 13/739,886.

GHB is present, for example, in the mammalian brain and other tissues. In the brain, the highest GHB concentration is found in the hypothalamus and basal ganglia and GHB is postulated to function as a neurotransmitter. The neuropharmacologic effects of GHB include increases in brain acetylcholine, increases in brain dopamine, inhibition of GABA-ketoglutarate transaminase and depression of glucose utilization but not oxygen consumption in the brain. GHB is converted to succinate and then metabolized via the Krebs cycle. Clinical trials have shown that GHB increases delta sleep and improves the continuity of sleep (Laborit, 1973; Lapierre et al., 1988; Lapierre et al., 1990; Yamada et al., 1967; Scharf, 1985).

GHB treatment substantially reduces the signs and symptoms of narcolepsy, i.e. excessive daytime sleepiness, cataplexy, sleep paralysis, apnea, narcolepsy, sleep time disturbances, hypnagogic hallucinations, sleep arousal, insomnia, and nocturnal myoclonus. In addition, GHB increases total sleep time and REM sleep, and it decreases REM latency (Mamelak et al, 1973; Yamada et al., 1967; Bedard et al., 1989), reduces sleep apnea (Scrima et al., 1987), and improves general anesthesia (Hasenbos and Gielen, 1985).

GHB has several clinical applications other than narcolepsy and sleep disorders. GHB has been reported to reduce alcohol craving, the number of daily drinks consumed, and the symptoms of alcohol withdrawal in patients (Gallimberti et al., 1989; Gallimberti et al., 1992; Gessa et al., 1992). GHB has been used to decrease the symptoms of opiate withdrawal, including both heroin and methadone withdrawal (Gallimberti et al., 1994; Gallimberti et al., 1993). It has analgesic effects that make it suitable as a pain reliever (U.S. Pat. No. 4,393,236). Intravenous administration of GHB has been reported to reduce intracranial pressure in patients (Strong, A. 1984). Also, administration of GHB was reported to increase growth hormone levels in patients (Gessa et al, 1994).

A good safety profile for GHB consumption, when used long term for treatment of narcolepsy has been reported. Patients have been safely treated for many years with GHB without development of tolerance (Scharf, 1985). Clinical laboratory tests carried out periodically on many patients have not indicated organ or other toxicities (Lammers, 1993; Scrima, 1990; Scharf, 1985; Mamelack, 1977; Mamelak, 1979; Gessa, 1992). The side effects of GHB treatment have been minimal in incidence and degree of severity, though they include sleepwalking, enuresis, headache, nausea and dizziness (Broughton and Mamelak, 1979; Mamelak et al., 1981; Mamelak et al., 1977; Scrima et al., 1989; Scrima et al., 1990; Scharf et al., 1985). Therefore, it is critical to identify adverse drug-drug interactions to maintain the positive safety profile for GHB.

GHB Pharmacology

GHB has at least two distinct binding sites (See Wu, et al., 2004) in the central nervous system. GHB is an agonist at the GHB receptor, which is excitatory, (Cash et al., 2009) and it is a weak agonist at the GABAB receptor, which is inhibitory. GHB acts in a similar fashion to some neurotransmitters in the mammalian brain and is probably synthesized from GABA in GABAergic neurons, and released when the neurons fire. If taken orally, GABA itself does not effectively cross the blood-brain-barrier. (See Kuriyama et al., 2005).

GHB induces the accumulation of either a derivative of tryptophan or tryptophan itself in the extracellular space, possibly by increasing tryptophan transport across the blood-brain barrier. The blood content of certain neutral amino-acids, including tryptophan, is also increased by peripheral GHB administration. GHB-induced stimulation of tissue serotonin turnover may be due to an increase in tryptophan transport to the brain and in its uptake by serotonergic cells. As the serotonergic system may be involved in the regulation of sleep, mood, and anxiety, the stimulation of this system by high doses of GHB may be involved in certain neuropharmacological events induced by GHB administration.

However, at therapeutic doses, GHB reaches much higher concentrations in the brain and activates GABAB receptors, which are primarily responsible for its sedative effects. (See Dimitrijevic et al., 2005). GHB's sedative effects are blocked by GABAB antagonists.

The role of the GHB receptor in the behavioral effects induced by GHB is more complex. GHB receptors are densely expressed in many areas of the brain, including the cortex and hippocampus, and these are the receptors that GHB displays the highest affinity for. There has been somewhat limited research into the GHB receptor; however, there is evidence that activation of the GHB receptor in some brain areas results in the release of glutamate, the principal excitatory neurotransmitter. Drugs that selectively activate the GHB receptor cause absence seizures in high doses, as do GHB and GABA(B) agonists. (See Banerjee et al., 1995.)

Activation of both the GHB receptor and GABA(B) is responsible for the addictive profile of GHB. GHB's effect on dopamine release is biphasic. (See Hechler et al., 1991). Low concentrations stimulate dopamine release via the GHB receptor. (See Maitre et al., 1990). Higher concentrations inhibit dopamine release via GABA(B) receptors as do other GABA(B) agonists such as baclofen and phenibut. (See Smolders et al., 1995). After an initial phase of inhibition, dopamine release is then increased via the GHB receptor. Both the inhibition and increase of dopamine release by GHB are inhibited by opioid antagonists such as naloxone and naltrexone. Dynorphin may play a role in the inhibition of dopamine release via kappa opioid receptors. (See Mamelak 1989).

This may explain the paradoxical mix of sedative and stimulatory properties of GHB, as well as the so-called "rebound" effect, experienced by individuals using GHB as a sleeping agent, wherein they awake suddenly after several hours of GHB-induced deep sleep. That is to say that, over time, the concentration of GHB in the system decreases below the threshold for significant GABAB receptor activation and activates predominantly the GHB receptor, leading to wakefulness. However, one embodiment of the present invention is the unexpected discovery that drugs change the PD profile of GHB to alter its effects and its safety profile. Example drugs are include valproate and diclofenac. It is important for efficacy safety purposes that the effect of GHB be maintained consistently and not subject to variation due to the effects of other drugs.

Both of the metabolic breakdown pathways shown for GHB can run in either direction, depending on the concentrations of the substances involved, so the body can make its own GHB either from GABA or from succinic semialdehyde. Under normal physiological conditions, the concentration of GHB in the body is rather low, and the pathways would run in the reverse direction to what is shown here to produce endogenous GHB. However, when GHB is consumed for recreational or health promotion purposes, its concentration in the body is much higher than normal, which changes the enzyme kinetics so that these pathways operate to metabolize GHB rather than produce it.

The pharmacokinetics of GHB have been investigated in alcohol dependent patients (Ferrara et al., 1992) and in normal healthy males (Palatini et al., 1993) after oral administration. GHB possesses a rapid onset and short pharmacological effect (Ferrara et al., 1992; Palatine et al., 1993; Lettieri and Fung, 1978; Arena and Fung, 1980; Roth and Giarman, 1966; Vickers, 1969; Lee, 1977). In alcohol dependent patients, GHB absorption into and elimination from the systemic circulation were fast processes. Virtually no unchanged drug could be recovered in the urine. There were preliminary indications that the pharmacokinetics of GHB might be non-linear or dose-dependent (Ferrara et al., 1992). In the healthy volunteers study, the pharmacokinetics of three rising GHB doses (12.5, 25, and 50 mg/kg) were investigated. These findings indicate that both the oral absorption and elimination processes of GHB were capacity-limited though the degree of dose dependency was moderate (Palatini et al., 1993).

Methods of making GHB salts are described, for example, in U.S. Pat. No. 4,393,236, and U.S. patent application Ser. No. 13/739,886 which are incorporated herein by reference.

It has been discovered that there are unexpected drug-drug interactions (DDI) between GHB and common drugs frequently prescribed for other ailments. It is one goal of the present invention to warn when those interactions may affect the safety profile of GHB. In one embodiment of the present invention, drugs that may affect GHB administration include valproate, diclofenac, and ibuprofen and combinations thereof.

GHB is a central nervous system (CNS) depressant. Alcohol and sedative hypnotics are contraindicated in patients who are using GHB. The concurrent use of GHB with other CNS depressants, including but not limited to opioid analgesics, benzodiazepines, sedating antidepressants or antipsychotics, general anesthetics, muscle relaxants, and/or illicit CNS depressants, may increase the risk of respiratory depression, hypotension, profound sedation, syncope, and death. If use of these CNS depressants in combination with GHB is required, dose reduction or discontinuation of one or more CNS depressants (including GHB) should be considered. In addition, if short-term use of an opioid (e.g. post- or periop- erative) is required, interruption of treatment with GHB should be considered. See the package insert for Xyrem®.

GHB may impair respiratory drive, especially with over-doses associated with interactions with other drugs and alcohol. Since valproate may potentiate the effect of GHB, a warning should accompany any use of valproate and GHB as stated herein. The warning should address the use of additional drugs that may further enhance the effect of GHB, such as alcohol or aspirin, for example.

Healthcare providers should caution patients about operating hazardous machinery, including automobiles or airplanes, until they are reasonably certain that GHB does not affect them adversely (e.g., impair judgment, thinking, or motor skills). Patients should not engage in hazardous occupations or activities requiring complete mental alertness or motor coordination, such as operating machinery or a motor vehicle or flying an airplane, for at least 6, 7, 8 or 9 hours after taking the second nightly dose of GHB. Patients should be queried about potential adverse events, such as excessive daytime sleepiness, CNS depression related events, etc. upon initiation of GHB therapy and periodically thereafter. These queries should include info regarding additional medication such as diclofenac and valproate for example. See the Xyrem® package insert.

In one embodiment described herein, patients are warned that combination of GHB with valproate can increase plasma levels and potentiate the activity of GHB and exacerbate all the effects and adverse event associated with GHB. These effects include the intended effects of drowsiness, sedation, and sleep and typically unintended events such as depressed respiration, CNS depression, excessive drowsiness, hepatic impairment, and depression, among other things.

In another embodiment, diclofenac mitigates and protects against the pharmcodynamic effects the effects of GHB. However, the mixture of GHB and diclofenac does not affect sleepiness and does not make a patient more attentive. Without wishing to be bound by theory, the effects may be due to the interaction between diclofenac and the GHB receptor in lieu of the MCT inhibitor activity.

Typical concentrations of GHB formulations are shown in U.S. Pat. Nos. 8,263,650 and 8,324,275, for example. They include minimum concentrations starting from 150 mg/ml to 450 mg/ml (at 10 mg/ml increments) and increasing to 600 mg/ml to 750 mg/ml (at 10 mg/ml increments) as a maximum. So, a broad range would include 150-750 mg/ml and any range within the broad range using 10 mg/ml increments. One embodiment of the invention is a range of 350-750 mg/ml and another is 450-550 mg/ml GHB. One embodiment of the present invention uses a GHB formulation with a pH range of 6-10, another uses a pH range of between 6.5-8. For example, a minimum concentration includes 350, 360, 370, 380 mg/ml, and so on up to at least 730, 740, and 750 mg/ml and all concentrations (measured in 10 mg/ml increments in between).

pH adjusting agents can include acids, bases and many of the compounds found in U.S. Pat. No. 8,263,650. In some embodiments the pH adjusting agent is an acid selected from the group of: acetic, acetylsalicylic, barbital, barbituric, benzoic, benzyl penicillin, boric, caffeine, carbonic, citric, dichloroacetic, ethylenediaminetetra-acetic acid (EDTA), formic, glycerophosphoric, glycine, lactic, malic, mandelic, monochloroacetic, oxalic, phenobarbital, phenol, picric, propionic, saccharin, salicylic, sodium dihydrogen phosphate, succinic, sulfadiazine, sulfamerazine, sulfapyridine, sulfathiazole, tartaric, trichloroacetic, and the like, or inorganic acids such as hydrochloric, nitric, phosphoric or sulfuric, and the like.

GHB is commercially available as a sodium salt, however, it can also be formulated as a mixture of salts as shown in U.S. Ser. No. 13/739,886, which is incorporated by reference as stated above. For example, the mixture comprises one, two, or three or more salts selected from the group consisting of a sodium salt of hydroxybutyrate (Na.GHB), a potassium salt of gamma-hydroxybutyrate (K.GHB), a magnesium salt of gamma-hydroxybutyrate (Mg.(GHB)$_2$), and a calcium salt of gamma-hydroxybutyrate (Ca.(GHB)$_2$). The different salts may be present in different percentages. For example, in certain embodiments, the pharmaceutical composition comprises Na.GHB, K.GHB, and Ca.(GHB)$_2$. In certain embodiments, the Na.GHB salt is present in a wt/wt % of about 5% to about 40%, the K.GHB salt is present in a wt/wt % of about 10% to about 40%, and the Ca.(GHB)$_2$ salt is present in a wt/wt % of about 20% to about 80%. In certain embodiments, the Na.GHB, K.GHB, and Ca.(GHB)$_2$ salts are present in a wt/wt % ratio of about 11%:39%:50%, respectively.

Valproic Acid

Valproic acid (VPA, also called valproate or divalproex), an acidic chemical compound, has found clinical use as an anticonvulsant and mood-stabilizing drug, primarily in the treatment of epilepsy, bipolar disorder, and, less commonly, major depression. See G. Rosenberg, Cell. Mol. Life. Sci. 64 (2007) 2090-2103. It is also used to treat migraine headaches and schizophrenia. A typical dose of valproate varies by indication. Dosages for seizures are between 10 to 15 mg/kg/day, with potential increases of 5 to 10 mg/kg/day. VPA is a liquid at room temperature, but it can be reacted with a base such as sodium hydroxide to form the salt sodium valproate, which is a solid. The acid, salt, or a mixture of the two (valproate semisodium, divalproate) are marketed under the various brand names Depakote, Depakote E R, Depakene, Depakene Crono (extended release in Spain), Depacon, Depakine, Valparin and Stavzor.

Valproate is believed to affect the function of the neurotransmitter GABA in the human brain, making it an alternative to lithium salts in treatment of bipolar disorder. Its mechanism of action includes enhanced neurotransmission of GABA (by inhibiting GABA transaminase, which breaks down GABA). However, several other mechanisms of action in neuropsychiatric disorders have been proposed for valproic acid in recent years. See Rosenberg G (2007). "The mechanisms of action of valproate in neuropsychiatric disorders: can we see the forest for the trees?". *Cellular and Molecular Life Sciences* 64 (16): 2090-103.

Valproic acid also blocks the voltage-gated sodium channels and T-type calcium channels. These mechanisms make valproic acid a broad-spectrum anticonvulsant drug. Valproic acid is an inhibitor of the enzyme histone deacetylase 1 (HDAC1), hence it is a histone deacetylase inhibitor. Valproic acid may interact with carbamazepine, as valproates inhibit microsomal epoxide hydrolase (mEH), the enzyme responsible for the breakdown of carbamazepine-10,11 epoxide (the main active metabolite of carbamazepine) into inactive metabolites. (See Gonzalez, Frank J.; Robert H. Tukey (2006). "Drug Metabolism". In Laurence Brunton, John Lazo, Keith Parker (eds.). Goodman & Gilman's The Pharmacological Basis of Therapeutics (11th ed.). New York: McGraw-Hill. pp. 79.) By inhibiting mEH, valproic acid causes a buildup of the active metabolite, prolonging the effects of carbamazepine and delaying its excretion. Valproic acid also decreases the clearance of amitriptyline and nortriptyline.

Aspirin may decrease the clearance of valproic acid, leading to higher-than-intended serum levels of the anticonvulsant. Also, combining valproic acid with the benzodiazepine clonazepam can lead to profound sedation and increases the risk of absence seizures in patients susceptible to them.

Valproic acid and sodium valproate reduce the apparent clearance of lamotrigine (lamictal). In most patients, the lamotrigine dosage for coadministration with valproate must be reduced to half the monotherapy dosage.

Valproic acid is contraindicated in pregnancy, as it decreases the intestinal reabsorption of folate (folic acid), which leads to neural tube defects. Because of a decrease in folate, megaloblastic anemia may also result. Phenyloin also decreases folate absorption, which may lead to the same adverse effects as valproic acid.

Valproic acid, 2-propylvaleric acid, is synthesized by the alkylation of cyanoacetic ester with two moles of propylbromide, to give dipropylcyanoacetic ester. Hydrolysis and decarboxylation of the carboethoxy group gives dipropylacetonitrile, which is hydrolyzed into valproic acid. See U.S. Pat. Nos. 3,325,361 and 4,155,929 and GB Pat. Nos. 980279 and 1522450. See also, T. R. Henry, "The History of Valproate in Clinical Neuroscience." Psychopharmacology bulletin (2003) 37 (Suppl 2):5-16.

Diclofenac

Diclofenac is a nonsteroidal anti-inflammatory drug (NSAID) taken to reduce inflammation and as an analgesic reducing pain in certain conditions. Diclofenac is used to treat pain, inflammatory disorders, and dysmenorrhea and is a commonly used NSAID. See Auler et al., Brazilian Jour. Med. Bio. Res., (1977) 30:369-374 and Hasan, et al., and Pakistan Jour. Pharmaceutical Sciences, vol. 18, No. 1, January 2005, pp 18-24 both are hereby incorporated by reference in their entireties.

The name is derived from its chemical name: 2-(2,6-dichloranilino) phenylacetic acid, it may be supplied as either the sodium or potassium salt. Diclofenac is available as a generic drug in a number of formulations; including Dichlofenac diethylammonium applied topically to joints. Over-the-counter (OTC) use is approved in some countries for minor aches and pains and fever associated with common infections.

Diclofenac is typically absorbed readily, but absorption is delayed upon administration with food. Its half-life varies from 1 to 3 hours with mean peak plasma levels of about 0.5 ug/ml to 1.0 ug/ml after 2 hours of a single dose of 25 mg. Diclofenac binds to human serum proteins, specifically albumin. See Hasan et al 2005.

Ibuprofen

Ibuprofen (from iso-butyl-propanoic-phenolic acid) is a nonsteroidal anti-inflammatory drug (NSAID) widely prescribed for pain relief, fever reduction, and swelling. Ibuprofen was derived from propanoic acid. Originally marketed as Brufen, ibuprofen is available under a variety of popular trademarks, including Motrin, Nurofen, Advil, and Nuprin. Ibuprofen is used primarily for fever, pain, dysmenorrhea and inflammatory diseases such as rheumatoid arthritis. It is also used for pericarditis and patent ductus arteriosus. It is a commonly used drug commercially available over the counter.

Nonsteroidal anti-inflammatory drugs such as ibuprofen work by inhibiting the enzyme cyclooxygenase (COX), which converts arachidonic acid to prostaglandin H2 (PGH2). PGH2, in turn, is converted by other enzymes to several other prostaglandins (which are mediators of pain, inflammation, and fever) and to thromboxane A2 (which stimulates platelet aggregation, leading to the formation of blood clots).

Like aspirin and indomethacin, ibuprofen is a nonselective COX inhibitor, in that it inhibits two isoforms of cyclooxygenase, COX-1 and COX-2. The analgesic, antipyretic, and anti-inflammatory activity of NSAIDs appears to operate mainly through inhibition of COX-2, whereas inhibition of COX-1 would be responsible for unwanted effects on the gastrointestinal tract. However, the role of the individual COX isoforms in the analgesic, anti-inflammatory, and gastric damage effects of NSAIDs is uncertain and different compounds cause different degrees of analgesia and gastric damage.

The synthesis of this compound consisted of six steps, started with the Friedel-Crafts acetylation of isobutylbenzene. Reaction with ethyl chloroacetate (Darzens reaction) gave the $\alpha,\beta$-epoxy ester, which was hydrolyzed and decarboxylated to the aldehyde. Reaction with hydroxylamine gave the oxime, which was converted to the nitrile, then hydrolyzed to the desired acid. See U.S. Pat. No. 3,385,886.

An improved synthesis by BHC required only three steps. After a similar acetylation, hydrogenation with Raney nickel gave the alcohol, which underwent palladium-catalyzed carbonylation.

Valproate, diclofenac, and ibruprofen are monocarboxylate transporter inhibitors. One embodiment of the present application is a method to improve safety by monitoring the combination of these compounds with GHB.

Monocarboxylate Transporters

Monocarboxylate transporters, or MCTs, constitute a family of proton-linked plasma membrane transporters that carry molecules having one carboxylate group (monocarboxylates), such as lactate and pyruvate, across biological membranes. See Halestrap A P, Meredith D (2004). "The SLC16 gene family-from monocarboxylate transporters (MCTs) to aromatic amino acid transporters and beyond". Pflugers Arch. 447 (5): 619-28.

MCTs are a series of transporters which move chemicals in body tissues, such as kidneys, blood/brain barrier, intestines, etc. They can transport chemical compounds back from urine to create a higher concentration in the blood than the urine. They can be used to treat an overdose or to prevent excretion of a compound. They can also be used to prevent absorption or transport into the brain or gut, or excretion via the urine. Exemplary MCT inhibitors include valproate, diclofenac, and ibubrofen.

Concomitant Administration of GHB and Drug-Drug Interactions

In one embodiment of the present invention the concomitant administration of MCT inhibitors, such as either valproate, diclofenac, or ibuprofen with GHB can effect GHB levels or activity and alter the GHB safety and efficacy profile to create an unsafe condition. For example, valproate can increase or prolong GHB effects and diclofenac can reduce or shorten GHB effects. For example, if the effects are increased, then there could be an increase of adverse events associated with too much GHB. Also, the effect of GHB may be prolonged to cause side effects, such as excessive daytime sleepiness (EDS), to last into the daytime. Prolongation of the effect would counter the purpose for providing the GHB and could create an unsafe situation for patients who wish to be alert and who may be engaged in otherwise dangerous activity. This concomitant administration can transform an otherwise safe dose of GHB into one with safety concerns. It is a health risk to patients and a medical challenge to health care workers.

The drug-drug interaction could also reduce the effects of GHB by altering its blood levels or otherwise. Reduction in the GHB level may also provide an unsafe condition due to excessive daytime sleepiness. In each situation, where GHB is increased, decreased or excessively cleared, those drug-drug interactions need to be identified to a health care worker to adjust the dose of GHB or discontinue the use of the other compound.

As recited on the product insert for Xyrem®, healthcare providers should caution patients about operating hazardous machinery, including automobiles or airplanes, until they are reasonably certain that GHB does not affect them adversely (e.g., impair judgment, thinking, or motor skills). Patients should not engage in hazardous occupations or activities requiring complete mental alertness or motor coordination, such as operating machinery or a motor vehicle or flying an airplane, for at least 6, 7, 8 or 9 hours after taking the second nightly dose of GHB.

In some embodiments in which diclofenac or valproate is discontinued to avoid an adverse drug interaction, they are discontinued within at least 3 days prior to or after starting GHB therapy. In various embodiments, diclofenac or valproate is discontinued within at least 4 days, or at least 5 days, or at least 6 days, or at least 7 days (or one week), or at least 8 days, or at least 9 days, or at least 10 days, or at least 11 days, or at least 12 days, or at least 13 days, or at least 14 days (or two weeks), or at least 15 days, or at least 16 days, or at least 17 days, or at least 18 days, or at least 19 days, or at least 20 days, or at least 21 days (or three weeks) prior to or after starting GHB therapy. In some embodiments, the diclofenac or valproate is discontinued no later than 2 weeks or 1 week before starting GHB therapy.

In some embodiments, a method of optimizing GHB therapy when valproate is provided comprises titrating the dosage of GHB administered to a patient downward relative to a previously administered dosage in the patient, so the dose does not result in an increased exposure to GHB. In some embodiments, a method of optimizing GHB therapy when diclofenac is provided comprises titrating the dosage of GHB administered to a patient upward relative to a previously administered dosage in the patient, so the dose results in an effective exposure to GHB.

Thus, the present invention includes a method for treating a patient who is suffering from excessive daytime sleepiness, cataplexy, sleep paralysis, apnea, narcolepsy, sleep time disturbances, hypnagogic hallucinations, sleep arousal, insomnia, and nocturnal myoclonus with a salt of gamma-hydroxybutyrate (GHB), wherein said patient is also being treated with valproate or diclofenac, comprising: administering to the patient a daily dose of a GHB salt wherein said daily dose is administered at an amount sufficient to reduce or eliminate such additive effects.

In one embodiment of the present invention, a reduced amount of GHB is administered to a patient when concomitantly administered with valproate. In another embodiment of the present invention, an increased amount of GHB is administered to a patient when concomitantly administered with diclofenac.

When valproate is concomitantly administered with GHB, The amount of GHB can be reduced at least 1%, 5%, 10%, 15%, 20%, 25%, 30%, 35%, 40%, 45%, or 50% of the normal dose of GHB. For example, if the normal dose is 9 g/day, then a dose that is adjusted to reduce the normal dose by 15% is 7.65 g/day. The GHB dose reduction may be taken for one or multiple GHB dosings. For example, GHB may be administered in two doses per night for narcolepsy. A typical adult range of doses for GHB are between 4.5 or 6 g as a minimum and 8 or 10 g/day as a maximum divided into two doses. The dose recommended on the package insert and approved by the FDA is between 4.5 and 9.0 g/day. Typical exemplary paediatric daily doses of GHB are between 1 g and 6 g/day for pediatric patients aged 0-6 years. Typical exemplary paediatric daily doses of GHB are between 1 g and 9 g/day for pediatric patients aged 7-17 years. However, these ranges are not absolute and can be increased or decreased by 1-2 grams in either direction. One dose is typically administered prior to bed (night time sleep) and another dose administered 1-2 hours later. See the Xyrem® package insert (Xyrem® is a registered trademark of Jazz Pharmaceuticals plc or its subsidiaries.). Either or both of the multiple doses may be reduced to present a safer administration profile. For example, the first dose may be reduced by the numbers referred to above or the second may be reduced by the same percentages, or both. Furthermore, the absolute amount of GHB per dose or per day may be reduced at least 0.5 g, 1 g, 1.5 g, 2.0 g, 2.5 g, 3.0 g, 3.5 g, or 4 g. An exemplary decrease in an adult dose would be to reduce the maximum dose to less than 8.5, 8, 7.5, 7, 6.5, 6, 5.5, 5, 4.5, 4, 3.5, 3 g/day and so on. The minimum dose will be reduced accordingly to 4, 3.5, 3, 2.5, 2, and so on.

In one embodiment of the present invention, diclofenac may dampen or delay the effect of GHB upon a patient during concomitant administration. In one embodiment, it may be useful to increase the amount of GHB that is administered to the patient. For example, GHB may be increased at least 1%, 5%, 10%, 15%, 20%, 25%, 30%, 35%, 40%, 45%, or 50% of the normal dose of GHB. For example, if the normal dose is 10 g/day, then a dose that is adjusted to increase the normal dose by 15% is 11.5 g/day. The GHB dose increase may be taken for one or multiple GHB dosings. For example, GHB may be administered in two doses per night for narcolepsy. Either, or both, of the multiple doses may be increased to present a safer administration profile. For example, the first dose may be increased by the numbers referred to above or the second may be increased by the same percentages, or both. Furthermore, the absolute amount of GHB per dose or per day may be increased at least 0.5 g, 1 g, 1.5 g, 2.0 g, 2.5 g, 3.0 g, 3.5 g, or 4 g. An exemplary increase in an adult dose would be to increase the minimum dose to 5, 5.5, 6, 6.5, 7, 7.5, 8, 8.5 g/day and so on. An increase in the maximum dose would be at least 9.5, 10, 10.5, 11, 11.5, 12, 12.5, 13, 13.5, 14 g/day and so on.

In another aspect, a package or kit is provided comprising GHB, optionally in a container, and a package insert, package label, instructions or other labelling including any one, two, three or more of the following information or recommendations: (a) use of diclofenac or valproate should be avoided or discontinued, (b) concomitant administration of GHB with drugs that are MCT inhibitors, such as diclofenac or valproate can alter the therapeutic effect or adverse reaction profile of GHB, (c) concomitant administration of GHB and valproate resulted in an increase in exposure to GHB, (d) concomitant administration of GHB and diclofenac resulted in a decrease in exposure to GHB, and/or (e) MCT inhibitors should be used with caution in patients receiving GHB due to the potential for increased GHB clearance.

Alternatively, diclofenac can be administered to counteract the effects of GHB toxicity using a reverse of the numerical relationships above. Similarly, valproate can be used to increase the effects of GHB in patients that cannot take higher amounts of GHB. In this regard, the present invention includes methods for reducing the effects of GHB toxicity in a patient in need thereof, comprising administering to said patient an effective amount of diclofenac such that potential toxic effects of GHB are reduced. The present invention also includes methods for potentiating the beneficial effects of GHB in a patient in need thereof comprising concomitantly administering to said patient an effective amount of valproate such that the beneficial effects of GHB are increased.

The examples below, which show drug interaction studies in healthy adults, demonstrated those instances, test conditions or metrics which showed a distinction between GHB and either of the test compounds, diclofenac, valproate, or ibuprofen. Additionally, drug interaction studies in healthy adults demonstrated pharmacokinetic or clinically significant pharmacodynamic interactions between GHB and diclofenac or valproate.

Example 1

This study was designed to compare Pharmacokinetic (PK) and Pharmacodynamic (PD) endpoints of Xyrem® sodium oxysorbate (GHB) with and without concomitant administration of diclofenac. A crossover design was employed to allow within-subject comparisons of the PK and PD of Xyrem® dosed alone and in combination with diclofenac. The PK and PD effects of Xyrem® upon those of diclofenac were also studied.

The PD parameters included a selection of automated tests of attention, information processing, working memory and skilled coordination from the CDR System. (Rapeport et al, 1996ab; Williams et al, 1996). (Wesnes et al, 1997). (Wesnes et al, 2000) (Modi et al, 2007).

Methods

This was a Phase 1, randomized, double-blind, placebo-controlled, three-period, crossover study in healthy subjects. 24 subjects were recruited to ensure that 18 completed the study. Following Screening and Baseline procedures, eligible subjects were entered into the study and received one of the following treatments per period, in randomized order:

Diclofenac placebo administered as one capsule qid (doses separated by 4 hours during the day, eg, approximately 8 am, 12 pm, 4 pm, and 8 pm) for 2 days before concomitant administration day. On concomitant administration day, one diclofenac placebo capsule administered at −1 h and 3 h, and 3 g of Xyrem® administered at 0 h and 4 h.

Diclofenac administered as 50 mg immediate-release (IR) tablet (overencapsulated) qid (doses separated by 4 hours during the day, eg, approximately 8 am, 12 pm, 4 pm, and 8 pm) for 2 days before concomitant administration day. On concomitant administration day, 50 mg diclofenac administered at −1 h and 3 h and 3 g of Xyrem® administered at 0 h and 4 h.

Diclofenac administered as 50 mg IR tablet (overencapsulated) qid (doses separated by 4 hours during the day, eg, approximately 8 am, 12 pm, 4 pm, and 8 pm) for 2 days before concomitant administration day. On concomitant administration day, 50 mg diclofenac administered at −1 h and 3 h and Xyrem® placebo (volume equivalent to 3 g of Xyrem® oral solution) administered at 0 h and 4 h.

Subjects were randomized to one of the above treatments on Day 1, crossed over to another treatment on Day 6, and crossed over again to the remaining treatment on Day 11 (Table 1). Subjects were dosed in groups of up to 12. A 2-day washout period followed each of the treatment periods. The treatments were as follows: A=Diclofenac placebo (qid 4 h apart on the 1st and 2nd day and 2 doses on the 3rd day of the period)+Xyrem® two 3 g doses 4 h apart on the 3rd day of the period. B=Diclofenac (50 mg qid 4 h apart on the 1st and 2nd day and 2 doses on the 3rd day of the period)+Xyrem® two 3 g doses 4 h apart on the 3rd day of the period. C=Diclofenac (50 mg qid 4 h apart on the 1st and 2nd day and 2 doses on the 3rd day of the period)+Xyrem® placebo two doses 4 h apart on the 3rd day of the period. PD parameters include the following: Cognitive Drug Research (CDR) System tasks: Karolinska Sleepiness Scale (KSS), Simple Reaction Time (SRT), Digit Vigilance (DV), Choice Reaction Time (CRT), Tracking and Numeric Working Memory (NWM).

Results

Power of attention-On this measure of focussed attention and information processing Xyrem® when co-dosed with diclofenac produced significantly less impairment than Xyrem® alone at 0.5 h; while the smaller impairments with the combination narrowly missed significance at 1 and 4.5 h. Xyrem® when co-dosed with diclofenac also resulted in impairments at two timepoints compared to diclofenac alone which at 6.5 h was significant and a trend at 8 h. See FIG. 1 which shows Change from Baseline Figure (LSmean with 95% CI) for Power of Attention (ms) (PD Completer Population).

Figure 2:
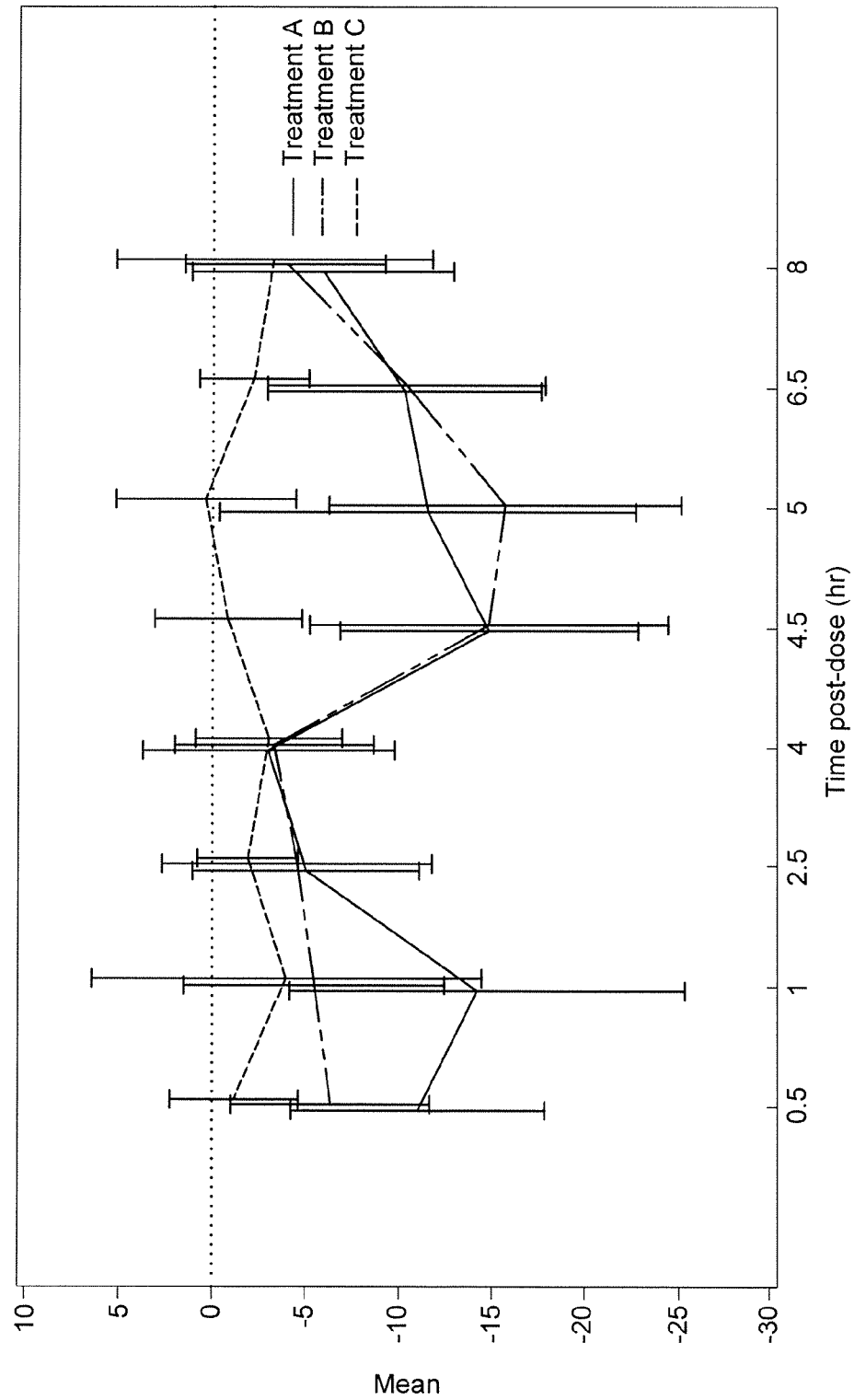
FIG. 2 shows change from baseline figure (LSmean with 95% CI) for Digit Vigilance Accuracy (%) (PD Completer Population).

Digit Vigilance Accuracy-On this measure of focussed attention Xyrem® when co-dosed with diclofenac produced significantly less impairment than Xyrem® alone at 1 and 2.5 h. See FIG. 2 which shows Change from Baseline Figure (LSmean with 95% CI) for Digit Vigilance Accuracy (%) (PD Completer Population).

Figure 3:
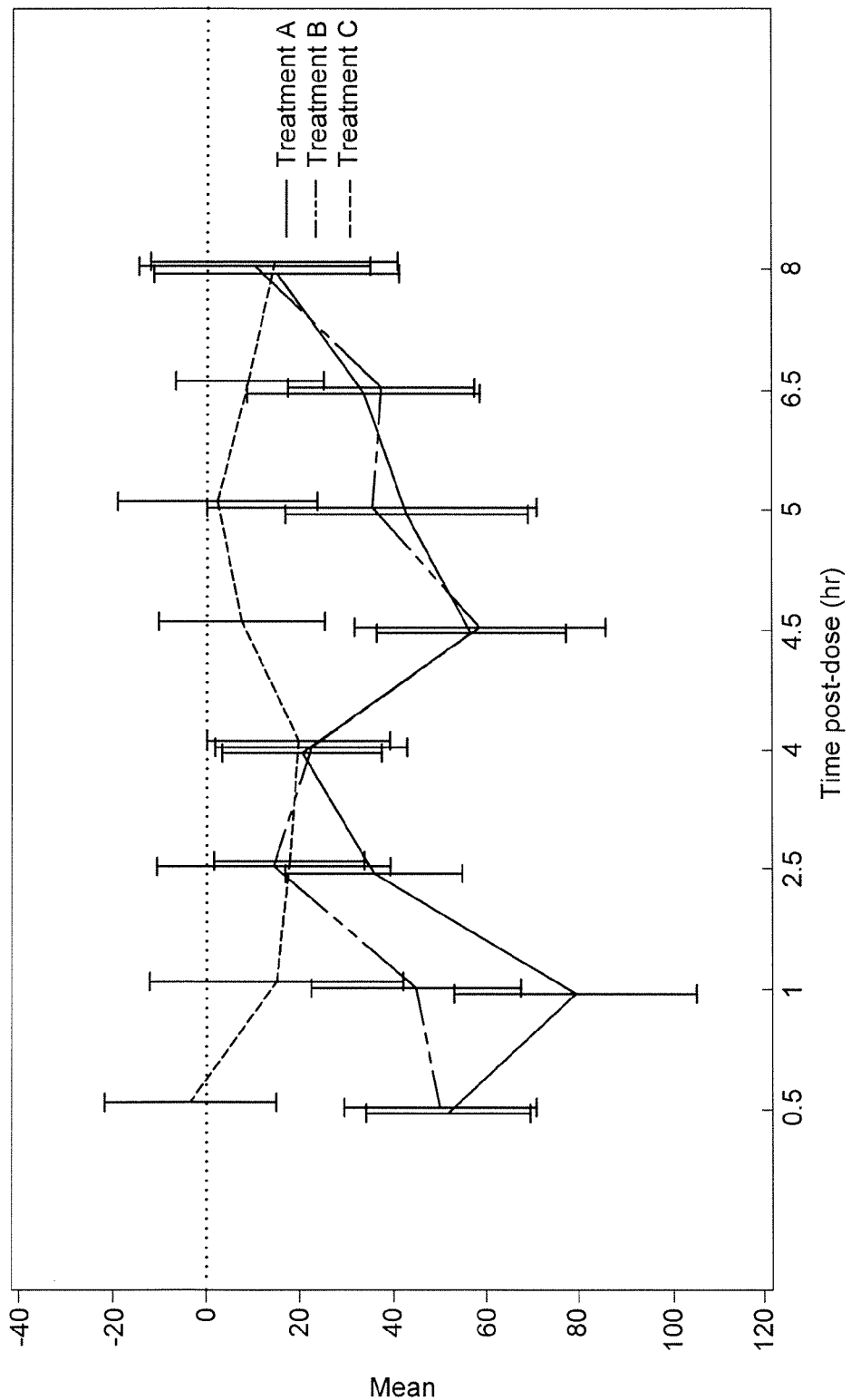
FIG. 3 shows change from baseline figure (LSmean with 95% CI) for Digit Vigilance Mean Reaction Time (ms) (PD Completer Population).

Digit Vigilance Mean Reaction Time—On this measure of focussed attention Xyrem® when co-dosed with diclofenac produced significantly less impairment than Xyrem® alone at 1 and 2.5 h. See FIG. 3 which shows Change from Baseline Figure (LSmean with 95% CI) for Digit Vigilance Mean Reaction Time (ms) (PD Completer Population).

Figure 4:
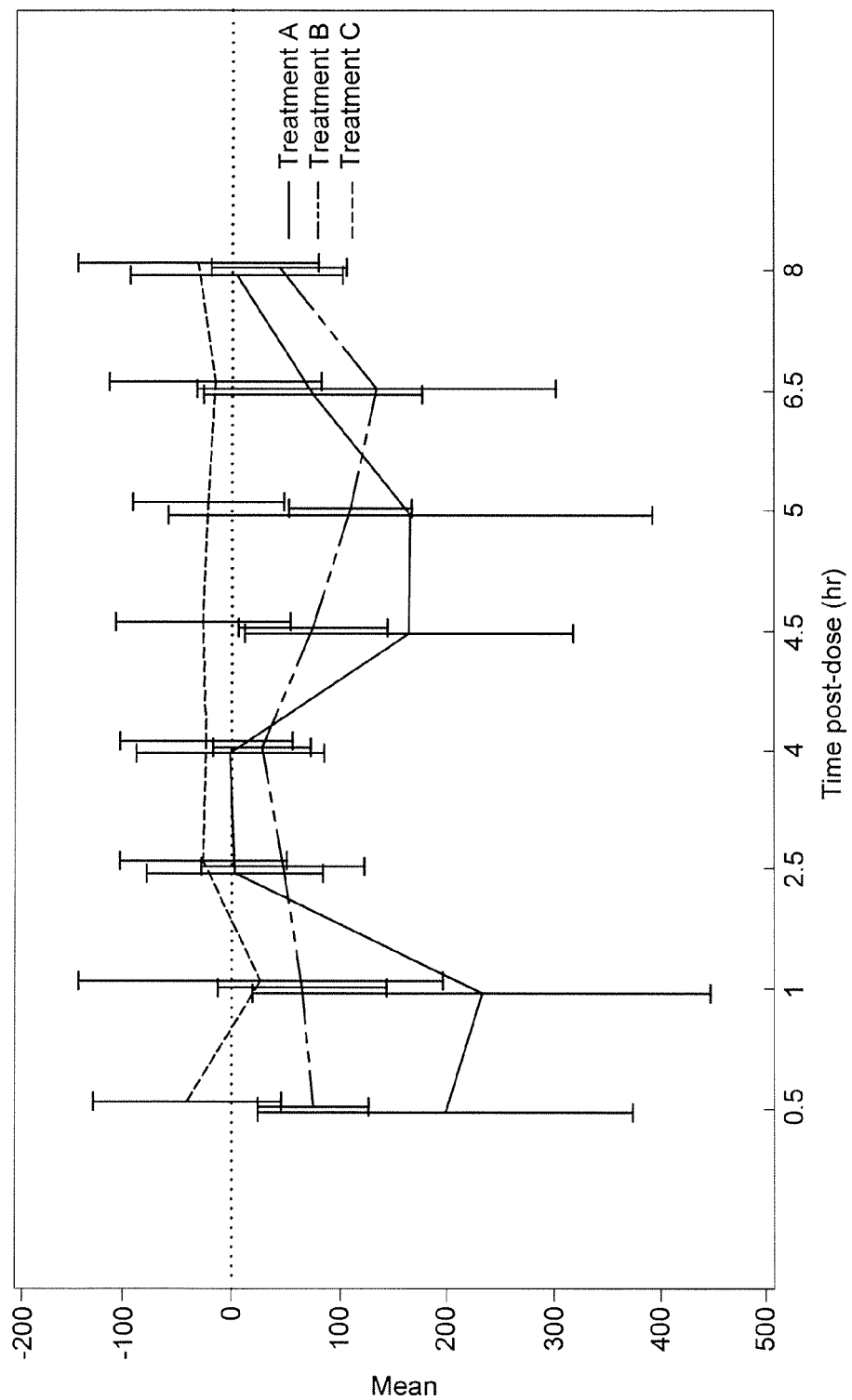
FIG. 4 shows change from baseline figure (LSmean with 95% CI) for Choice Reaction Time Mean (ms) (PD Completer Population).

Choice Reaction Time Mean-Impairments to this measure of attention and information processing were significantly smaller than with Xyrem® alone when co-dosed with diclofenac during the hour following the first dose of Xyrem®. See FIG. 4 which shows Change from Baseline Figure (LSmean with 95% CI) for Choice Reaction Time Mean (ms) (PD Completer Population).

While diclofenac alone had no effect on sleepiness or cognitive function, when co-dosed with Xyrem® it significantly reduced the effects of the compound on Power of Attention and two of the contributing scores, simple and choice reaction time; these effects being seen during the hour after the first dose of Xyrem®. On the other hand, there was no evidence on any measure of greater cognitive impairment or sleepiness when the two compounds were co-dosed.

The extent of the reductions in the impairments to the ability to focus attention and efficiently process information were quite notable, and likely to be of clinical relevance. It is interesting that protective effect of diclofenac was not seen on the subjects ratings of alertness, such a dissociation having been seen previously with haloperidol in healthy elderly volunteers (Beuzan et al, 1991).

In conclusion, evidence of an interaction was seen in this study over the hour following the first dose of Xyrem® on the study days, the impairments being notably smaller when diclofenac was co-dosed with Xyrem®. There was no interaction however on the feelings of sleepiness in the subjects.

Example 2

This study is designed to compare the pharmacokinetic (PK) and pharmacodynamic (PD) endpoints of Xyrem® with and without co-administration of divalproex sodium extended-release tablets. The crossover design allows within-subject comparisons of the PK and PD of Xyrem® dosed alone and in combination with divalproex sodium extended-release tablets. PD parameters include the following: Cognitive Drug Research (CDR) System tasks: Karolinska Sleepiness Scale (KSS), Simple Reaction Time (SRT), Digit Vigilance (DV), Choice Reaction Time (CRT), Tracking and Numeric Working Memory (NWM).

The objectives of this study were to evaluate the PK and PD of Xyrem® co-administered with divalproex sodium extended-release tablets and to evaluate and compare the safety and tolerability of Xyrem® with and without co-administration of divalproex sodium extended-release tablets.

This was a Phase 1, randomized, double-blind, placebo-controlled, five-period, crossover study in healthy male subjects. The study was conducted in approximately 24 healthy subjects to ensure completion of 16 subjects. Following Screening and Baseline procedures, eligible subjects were randomized to receive Xyrem® and Xyrem® placebo in a crossover fashion in Periods 1 and 2; were dosed with divalproex sodium extended-release tablets for 10 consecutive days in Period 3; and while continuing to take divalproex sodium extended-release tablets, were randomized to receive Xyrem® and Xyrem® placebo in a crossover fashion in Periods 4 and 5 (Table 1).

Periods 1 and 2:

Subjects were randomized to receive two 3 g doses of Xyrem® or Xyrem® placebo 4 hours apart in a crossover fashion at approximately 9 AM (first dose) and 1 PM (second dose) on Days 1 and 3. PK and PD parameters were evaluated during the 24 hours postdose.

Blood samples (4 mL) for sodium oxybate concentrations were collected at predose and at specified time-points up to 12 hours after the first dose of Xyrem® or Xyrem® placebo on Days 1 and 3. A PD Battery including the Karolinska Sleepiness Scale, Simple Reaction Time task, Digit Vigilance task, Choice Reaction Time task, Tracking task, and Numeric Working Memory task was administered at planned time-points up to X hours after first dose (X hours after second dose), and safety were monitored at specified timepoints on Days 1 and 3 as well as throughout the periods.

Period 3:

All subjects received divalproex sodium extended-release tablets 1250 mg at approximately 8 AM on Days 5 through 14. Blood samples (4 mL) for valproic acid concentrations were collected before the divalproex sodium dose (to determine trough concentration for assessment of steady state) on Days 13 and 14. Safety was monitored at specified timepoints as well as throughout the period.

Periods 4 and 5:

Subjects continued taking 1250 mg divalproex sodium extended-release tablets at approximately 8 AM on Days 15 through 18. Subjects were also randomized to receive two 3 g doses of Xyrem® or Xyrem® placebo in a crossover fashion at approximately 9 am (first dose) and 1 pm (second dose) on Days 15 and 18. The first dose of Xyrem® or Xyrem® placebo was taken approximately 1 hour after dosing with divalproex sodium extended-release tablets, and the second dose of Xyrem® or Xyrem® placebo was taken 4 hours after the first Xyrem®/Xyrem® placebo dose.

Blood samples (4 mL) to measure plasma sodium oxybate concentrations were collected at pre Xyrem®/Xyrem® placebo dose and at specified timepoints after the first Xyrem® or Xyrem® placebo dose on Days 15 and 18. Blood samples (4 mL) to measure plasma valproic acid concentrations were collected pre divalproex sodium dose and at specified timepoints after the dose of divalproex sodium extended-release tablets on Day 15 and 18.

The PD battery was administered on Day 15 and 18, and safety was monitored at specified times on Days 15 and 18 as well as throughout the periods.

The treatments were as follows: A=Xyrem®, two 3 g doses, 4 hours apart at approximately 9 AM ($1^{st}$ dose) and 1

PM (2nd dose); B=Xyrem® placebo, two doses, 4 hours apart; and C=Divalproex sodium 1250 mg, once a day at approximately 8 AM.

Results

The results below show the tests in which GHB administration was affected by concomitant administration of any of three MCT inhibitors, such as valproate, diclofenac, and ibubrofen.

Continuity of Attention

Figure 5:
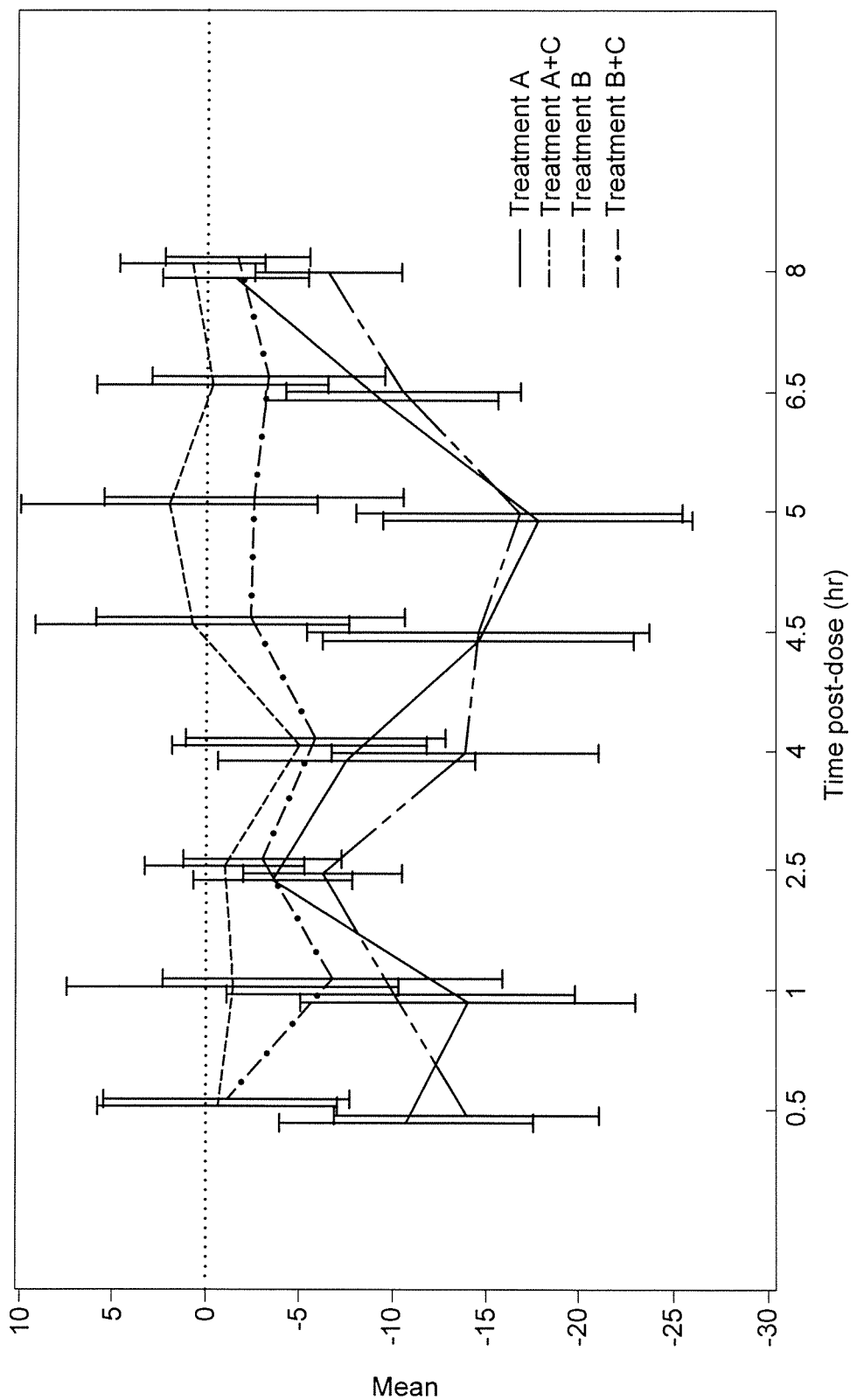
FIG. 5 shows change from baseline figure (LSmean with 95% CI) for Continuity of Attention (#) (PD Population). Treatment A=Xyrem®. Treatment B=Xyrem® placebo. Treatment C=valproate.

Xyrem® and divalproex sodium together (A+C) when compared to Xyrem® alone (A) showed a slightly delayed recovery for the combination at 4 hours and 8 hours. See FIG. 5 which shows Change from Baseline Figure (LSmean with 95% CI) for Continuity of Attention (#) (PD Population).

Simple Reaction Time Mean

Figure 6:
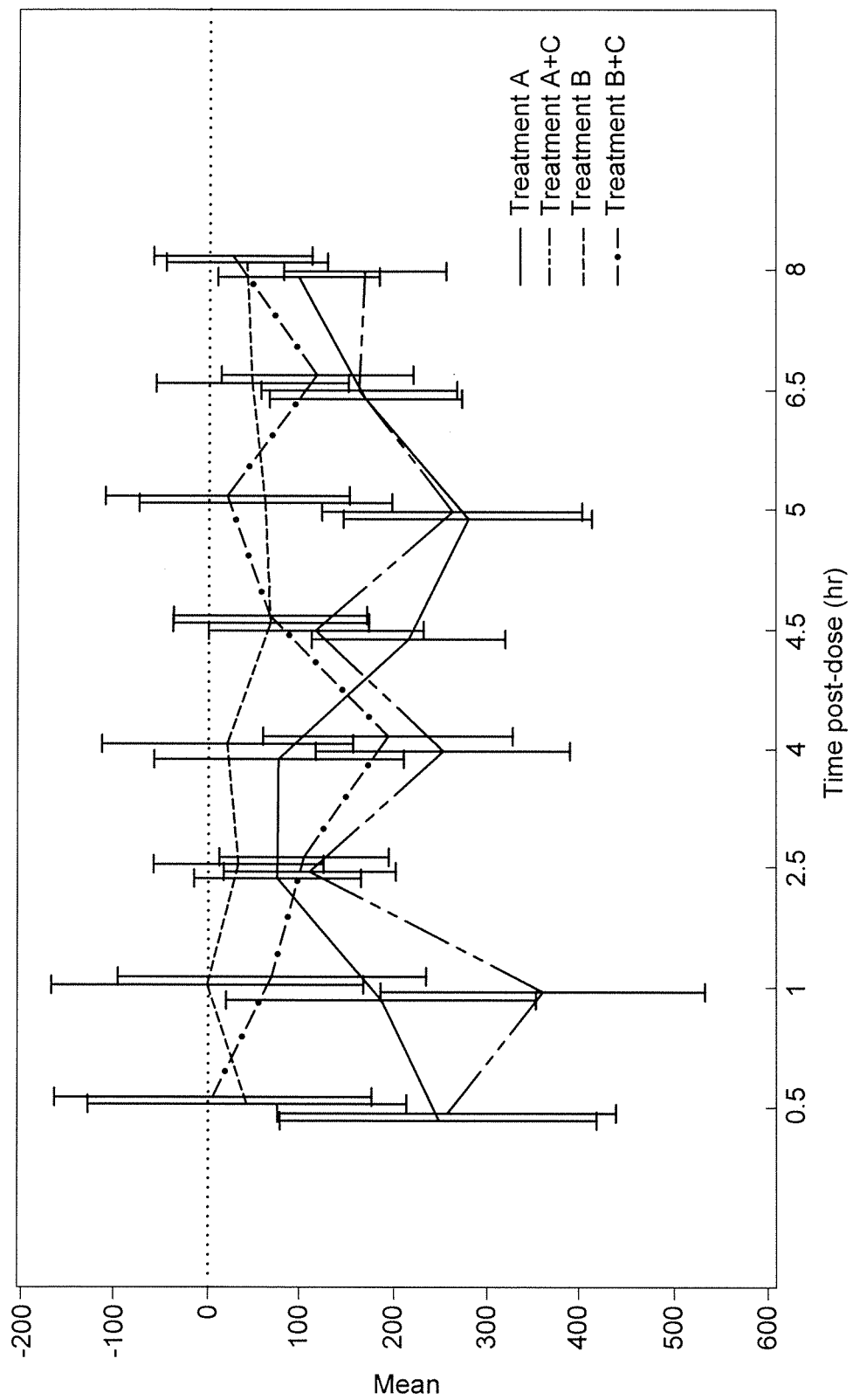
FIG. 6 shows change from baseline figure (LSmean with 95% CI) for Simple Reaction Time Mean (ms) (PD Population).

At 1 hour and 4 hours, Xyrem® and divalproex sodium together produced statistically reliably greater impairments than Xyrem® alone. See FIG. 6, which shows Change from Baseline Figure (LSmean with 95% CI) for Simple Reaction Time Mean (ms) (PD Population).

Digit Vigilance Accuracy

Figure 7:
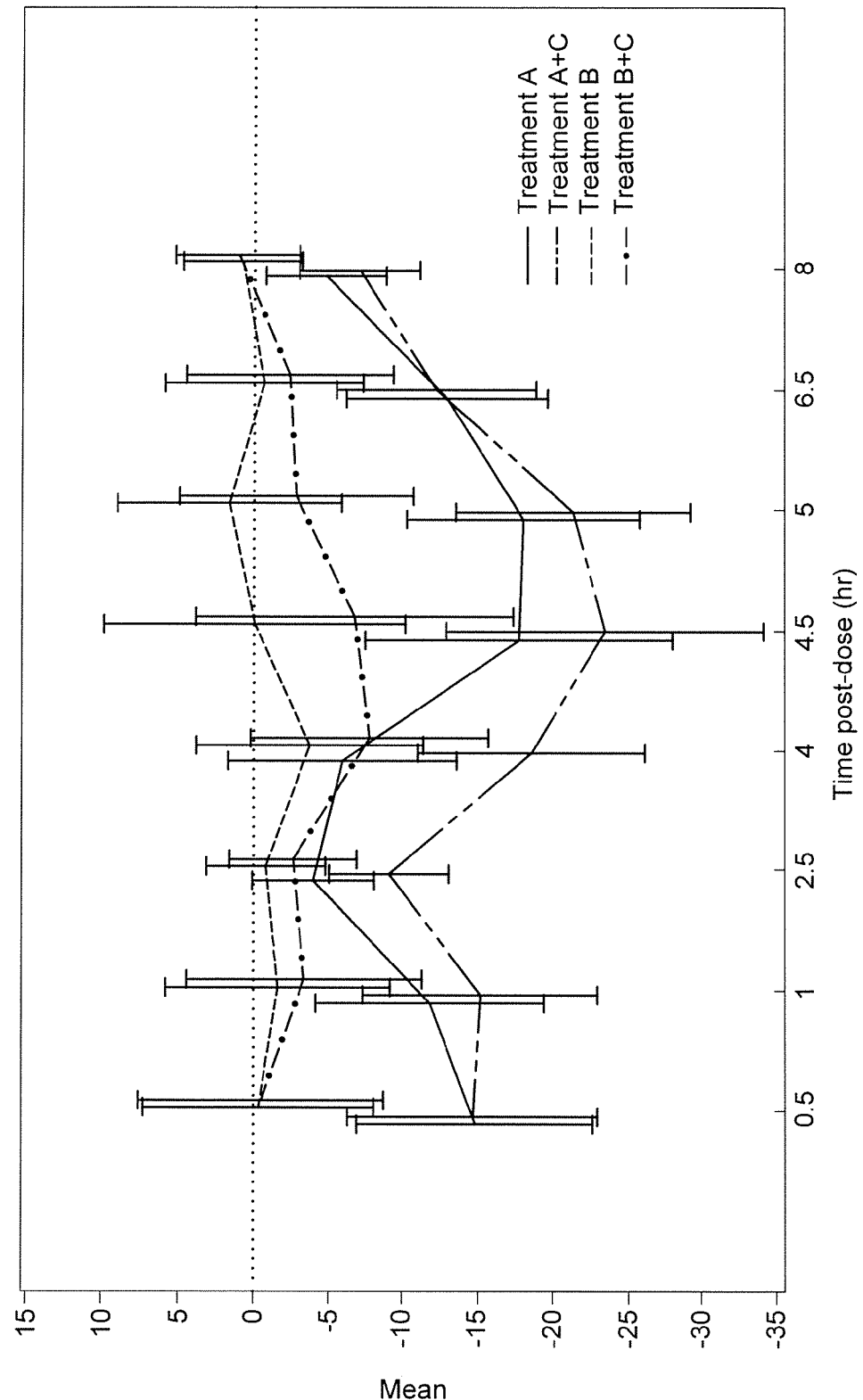
FIG. 7 shows change from baseline figure (LSmean with 95% CI) for Digit Vigilance Accuracy (%) (PD Population).

At 2.5 and 4 hours Xyrem® and divalproex sodium together were statistically reliably different greater impairment to Xyrem® alone. See FIG. 7, which shows Change from Baseline Figure (LSmean with 95% CI) for Digit Vigilance Accuracy (%) (PD Population).

Tracking Distance from Target

Figure 8:
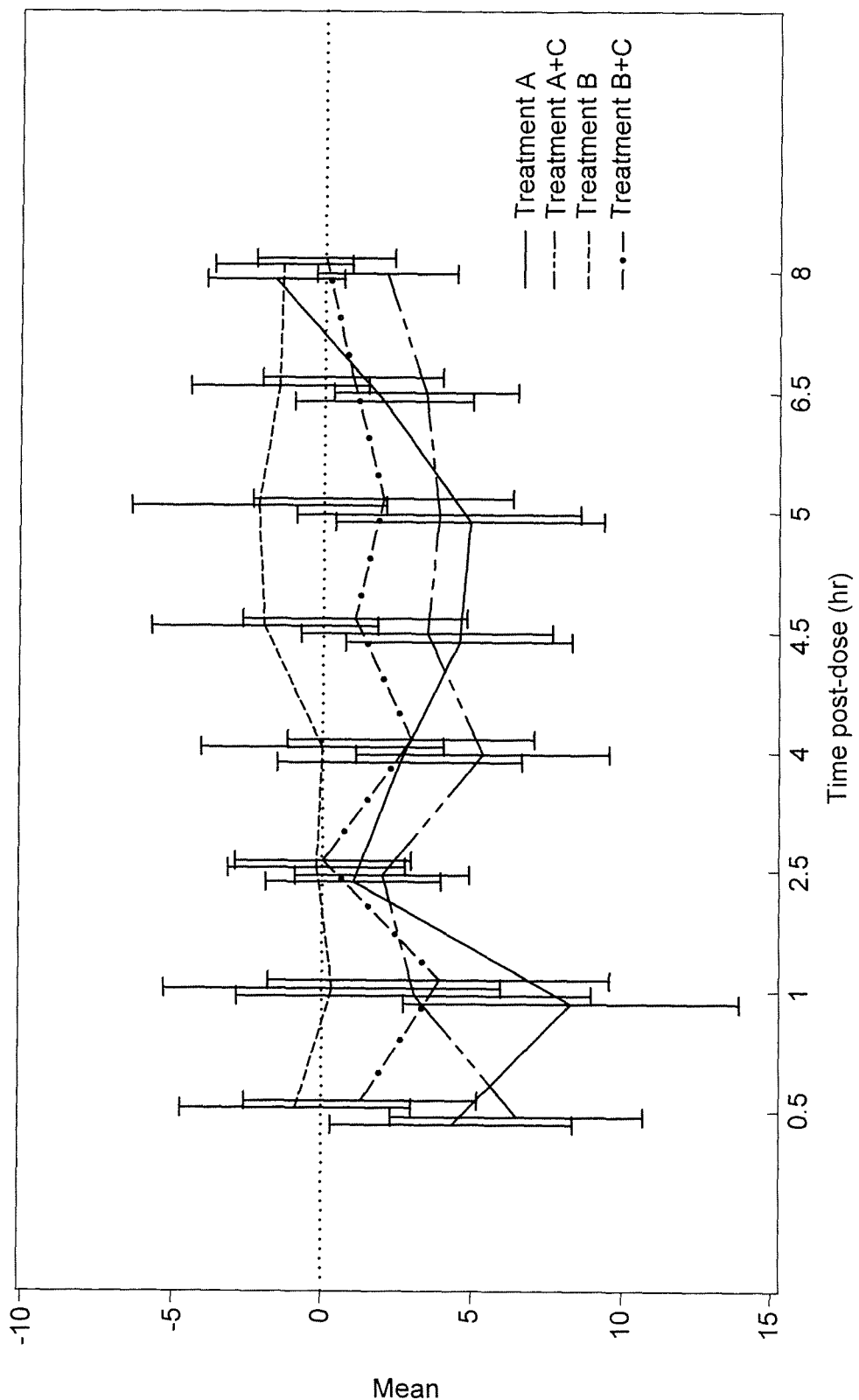
FIG. 8 shows change from baseline figure (LSmean with 95% CI) for Tracking Distance from Target (mm) (PD Population).

Xyrem® and divalproex sodium together (A+C) when compared to Xyrem® alone (A) showed a statistically significant difference by a slightly delayed recovery for the combination at 4 and 8 hours. See FIG. 8 which shows the Change from Baseline Figure (LSmean with 95% CI) for Tracking Distance from Target (mm) (PD Population).

Numeric Working Memory Sensitivity Index

Figure 9:
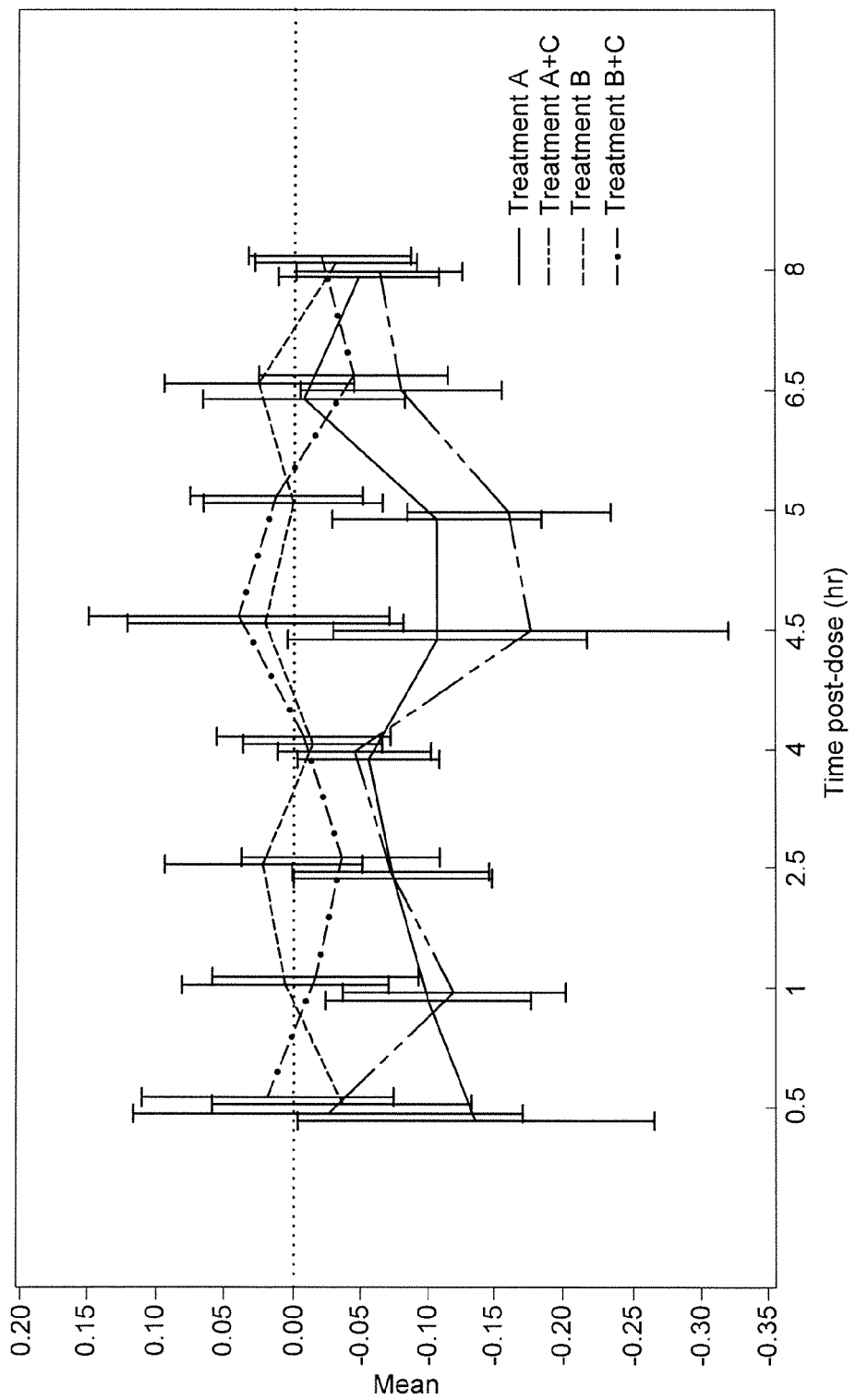
FIG. 9 shows change from baseline figure (LSmean with 95% CI) for Numeric Working Memory Sensitivity Index (#) (PD Population).

Xyrem® and divalproex sodium together (A+C) when compared to Xyrem® alone (A) showed a difference at 4.5 through 8 hours. See FIG. 9, which shows the Change from Baseline Figure (LSmean with 95% CI) for Numeric Working Memory Sensitivity Index (#) (PD Population).

Numeric Working Memory Mean Reaction Time

Figure 10:
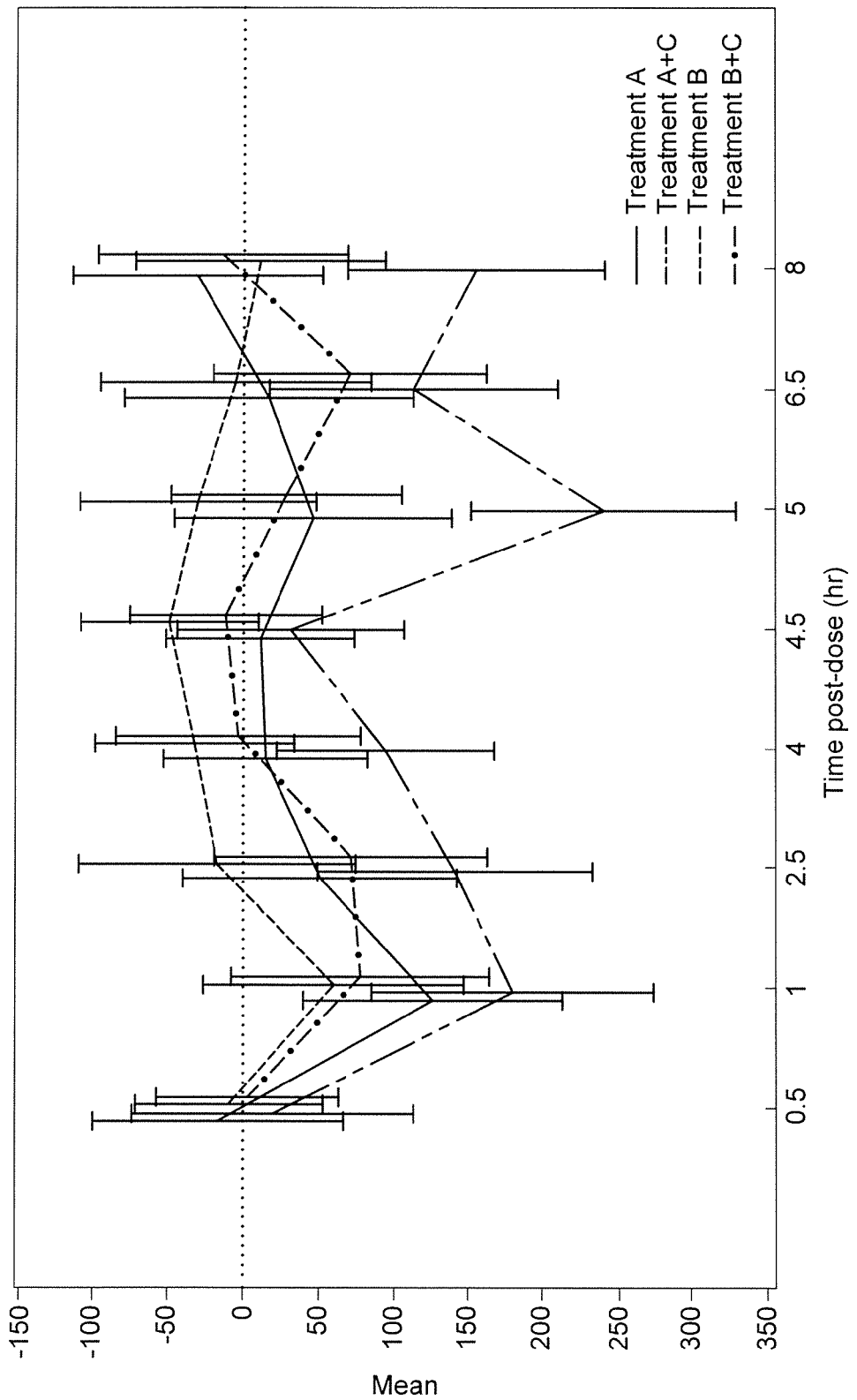
FIG. 10 shows change from baseline figure (LSmean with 95% CI) for Numeric Working Memory Mean Reaction Time (ms) (PD Population).

Xyrem® and divalproex sodium together (A+C) when compared to Xyrem® alone (A) showed statistically significant differences at 2.5, 5 and 8 hours when the combination produced greater impairment. See FIG. 10, which shows the Change from Baseline Figure (LSmean with 95% CI) for Numeric Working Memory Mean Reaction Time (ms) (PD Population).

In addition, it was observed that renal excretion of GHB increase 30% upon co-administration of Valproate.

We also found pk changes which were consistent with the inhibition of GHB dehydrogenase. This effect will increase the exposure of GHB to the subject and increase $C_{max}$ and AUC about 15%.

The combination of Xyrem® dosed with divalproex sodium was compared to divalproex sodium alone, more consistent statistically significant impairments over time were seen with the combination, than when Xyrem® was compared to its placebo, indicating that the effects of co-administration, when they appeared, were in the direction of increased impairments.

As has been seen previously, Xyrem® induces sleepiness and produces impairments to attention, working memory and performance on a tracking task in healthy volunteers. Divalproex sodium alone showed no consistent or notable effects on cognitive function or sleepiness. There were occasions when co-administration of Xyrem® and divalproex sodium produced greater deficits than Xyrem® alone. Further the combination also produced more consistent impairments when compared with divalproex sodium alone, than did Xyrem® when compared to its placebo. Thus this study has found evidence that co-administration of Xyrem® and divalproex produces greater impairments to cognitive function and sleepiness than were seen with Xyrem® alone.

Example 3

The effects of Ibuprofen were evaluated when combined with Xyrem® in a manner similar to the above. No differences were seen using the metrics above for Karolinska Sleepiness Scale (KSS), and the following CDR System tasks: Simple Reaction Time, Digit Vigilance, Choice Reaction Time, Tracking and Numeric Working Memory. However, it was observed that renal excretion of Xyrem® doubled upon concomitant administration of Ibuprofen and Xyrem®.

All publications and patent applications cited in this specification are herein incorporated by reference as if each individual publication or patent application were specifically and individually indicated to be incorporated by reference. Although the foregoing has been described in some detail by way of illustration and example for purposes of clarity of understanding, it will be readily apparent to those skilled in the art in light of the teachings of the specification that certain changes and modifications may be made thereto without departing from the spirit or scope of the appended claims.

What is claimed is:

1. A method for treating a patient who is suffering from excessive daytime sleepiness, cataplexy, sleep paralysis, apnea, narcolepsy, sleep time disturbances, hypnagogic hallucinations, sleep arousal, insomnia, or nocturnal myoclonus with gamma-hydroxybutyrate (GHB) or a salt thereof, said method comprising:
   orally administering to the patient in need of treatment at least a 5% increase in an effective dosage amount between 1 gram and 10 grams per day of the GHB or salt thereof when the patient is receiving a concomitant administration of diclofenac or a salt thereof.

2. The method in accordance with claim 1, wherein there is at least about a 15% increase in the effective dosage amount of the GHB or salt thereof normally given to the patient.

3. The method in accordance with claim 2, wherein the dose of GHB or salt thereof given to the patient without concomitant administration of diclofenac is a range between 4.5 to 9 grams per day.

4. The method in accordance with claim 1, wherein the effective dosage amount is increased between the range of about 5% to 10%, about 10% to 15%, about 15% to 20%, about 20% to 25%, about 25% to 30%, about 30% to 35%, about 35% to 40%, about 40% to 45%, or about 45% to 50%, relative to the dose of the GHB or salt thereof normally given to the patient.

5. The method in accordance with claim 1, wherein the patient is suffering from narcolepsy.

6. The method in accordance with claim 1, wherein the effective dosage amount is increased from a range of between 4.5 to 9 grams per day.

7. The method in accordance with claim 1, wherein the amount of GHB or salt thereof administered to the patient is between 7 grams and 12 grams per day after the increase.

8. The method in accordance with claim 1, wherein the amount of GHB or salt thereof administered to the patient is between 9 grams and 11 grams per day after the increase.

9. A method of safely administering GHB or a salt thereof for excessive daytime sleepiness, cataplexy, sleep paralysis, apnea, narcolepsy, sleep time disturbances, hypnagogic hallucinations, sleep arousal, insomnia, or nocturnal myoclonus in a human patient who is being administered GHB, said method comprising:
- determining if the patient has taken, or will take, a concomitant dose of diclofenac or a salt thereof; and
- orally administering an increased amount of the GHB or salt thereof to the patient wherein the increase is at least 5% compared to a dose without concomitant administration of diclofenac or salt thereof that is between 1 gram and 10 grams per day.

10. The method in accordance with claim 9, wherein the amount of GHB or salt thereof administered to the patient is increased at least 15%.

11. The method in accordance with claim 9, wherein the diclofenac or salt thereof is administered within two weeks of administration of the GHB or salt thereof.

12. The method in accordance with claim 9, wherein the diclofenac or salt thereof is administered within three days of administration of the GHB or salt thereof.

13. The method in accordance with claim 9, wherein the patient is suffering from narcolepsy.

14. The method in accordance with claim 9, further comprising recommending to increase the starting dose by 20%.

15. A method for treating a patient who is suffering from narcolepsy, said method comprising:
- administering a therapeutically effective amount of a formulation containing a GHB salt to a patient at between 1 gram and 10 grams per day and at a concentration of between 350 and 750 mg/ml with a pH of between 6 and 10;
- determining if the patient is also being administered diclofenac or a salt thereof;
- warning of a potential drug/drug interaction due to the combination of diclofenac or a salt thereof and the GHB salt; and
- recommending increasing the dose of the GHB salt at least 15%.

16. The method in accordance with claim 15, wherein the diclofenac or salt thereof is administered within two weeks of administration of the GHB salt.

17. The method in accordance with claim 15, wherein the diclofenac or a salt thereof is administered within three days of administration of the GHB salt.

18. The method in accordance with claim 15, wherein the GHB salt is administered at a concentration of between 450 to 550 mg/ml.

19. The method in accordance with claim 18, further comprising adding water to the GHB salt formulation.

20. The method in accordance with claim 15, wherein the GHB salt formulation has a pH between 6.5 and 8.

21. The method in accordance with claim 15, further comprising administering the increased dose of the GHB salt to the patient.

22. The method in accordance with claim 15, wherein the GHB salt comprises a single salt or a mixture of salts of GHB selected from the group consisting of a sodium salt of hydroxybutyrate (Na•GHB), a potassium salt of gamma-hydroxybutyrate (K•GHB), a magnesium salt of gamma-hydroxybutyrate (Mg•(GHB)$_2$), and a calcium salt of gamma-hydroxybutyrate (Ca•(GHB)$_2$).

23. The method in accordance with claim 15, wherein the dose of GHB or salt thereof without concomitant administration of diclofenac is a range between 4.5 to 9 grams per day.

24. The method in accordance with claim 15, comprising recommending increasing a starting dose at least 20%.

25. The method in accordance with claim 15, further comprising adding water to the GHB salt formulation.

26. The method in accordance with claim 15, further comprising optionally diluting the GHB salt formulation from a starting concentration of between 350 and 750 mg/ml with a pH of between 6 and 10.

27. A method for treating a patient who is suffering from narcolepsy, said method comprising:
- orally administering a therapeutically effective amount of a formulation containing a GHB salt;
- determining if the patient is also being administered diclofenac or salt thereof;
- recommending a 20% increase in the starting dose of the GHB salt such that the amount that the patient is administered is increased to about 5.4 grams GHB per day.

28. The method in accordance with claim 27, further comprising optionally diluting the GHB salt formulation from a starting concentration of between 350 and 750 mg/ml with a pH of between 6 and 10.

* * * * *